United States Patent
Apte et al.

(10) Patent No.: US 10,246,753 B2
(45) Date of Patent: *Apr. 2, 2019

(54) METHOD AND SYSTEM FOR CHARACTERIZING MOUTH-ASSOCIATED CONDITIONS

(71) Applicant: uBiome, Inc., San Francisco, CA (US)

(72) Inventors: Zachary Apte, San Francisco, CA (US); Catalina Valdivia, San Francisco, CA (US); Daniel Almonacid, San Francisco, CA (US); Jessica Richman, San Francisco, CA (US)

(73) Assignee: uBiome, Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/452,529

(22) Filed: Mar. 7, 2017

(65) Prior Publication Data

US 2017/0175172 A1   Jun. 22, 2017

Related U.S. Application Data

(63) Continuation-in-part of application No. 15/097,862, filed on Apr. 13, 2016, now Pat. No. 9,710,606.

(60) Provisional application No. 62/146,810, filed on Apr. 13, 2015, provisional application No. 62/146,833, filed on Apr. 13, 2015, provisional application No. 62/147,124, filed on Apr. 14, 2015, provisional application No. 62/146,852, filed on Apr. 13, 2015, provisional application No. 62/147,058, filed on Apr. 14, 2015, provisional application No. 62/147,077, filed on Apr. 14, 2015, provisional application No. 62/147,315, filed on Apr. 14, 2015, provisional application No. 62/147,337, filed on Apr. 14, 2015, provisional application No. 62/304,642, filed on Mar. 7, 2016, provisional application No. 62/304,645, filed on Mar. 7, 2016.

(51) Int. Cl.

| | |
|---|---|
| *G01N 33/48* | (2006.01) |
| *C12Q 1/689* | (2018.01) |
| *G01N 33/487* | (2006.01) |
| *G06F 19/24* | (2011.01) |
| *G06F 19/00* | (2018.01) |
| *C40B 30/02* | (2006.01) |
| *G06F 19/28* | (2011.01) |
| *G16H 50/20* | (2018.01) |
| *G06G 7/58* | (2006.01) |

(52) U.S. Cl.
CPC ............. *C12Q 1/689* (2013.01); *C40B 30/02* (2013.01); *G01N 33/48792* (2013.01); *G06F 19/24* (2013.01); *G06F 19/28* (2013.01); *G06F 19/3418* (2013.01); *G06F 19/3481* (2013.01); *G16H 50/20* (2018.01); *C12Q 2600/106* (2013.01); *C12Q 2600/112* (2013.01); *C12Q 2600/16* (2013.01); *Y02A 90/26* (2018.01)

(58) Field of Classification Search
None
See application file for complete search history.

(56) References Cited

U.S. PATENT DOCUMENTS

| | | |
|---|---|---|
| 521,843 A | 6/1894 | Baker |
| 6,033,864 A | 3/2000 | Braun et al. |
| 6,309,643 B1 | 10/2001 | Braun et al. |
| 6,632,641 B1 | 10/2003 | Brennan et al. |
| 6,861,053 B1 | 3/2005 | Lin et al. |
| 7,048,906 B2 | 5/2006 | Lin et al. |
| 7,176,002 B2 | 2/2007 | Lao et al. |
| 8,478,544 B2 | 7/2013 | Colwell et al. |
| 8,598,203 B2 | 12/2013 | Tarcic et al. |
| 8,883,264 B2 | 11/2014 | Yang et al. |
| 9,028,841 B2 | 5/2015 | Henn et al. |

(Continued)

FOREIGN PATENT DOCUMENTS

| | | |
|---|---|---|
| CN | 105407728 | 3/2015 |
| EP | 2631240 | 8/2013 |

(Continued)

OTHER PUBLICATIONS

"K03100: lepB: signal pepidase I,"KEGG, Aug. 7, 2012 (Aug. 7, 2012), p. 1 of 1. Retrieved from the Internet: on Jun. 12, 2016 (Jun. 12, 2016).

(Continued)

*Primary Examiner* — Eric S Dejong
(74) *Attorney, Agent, or Firm* — Kilpatrick Townsend & Stockton LLP

(57) ABSTRACT

Embodiments of a system and method for characterizing a mouth-associated condition in relation to a user can include one or more of: a handling network operable to collect containers including material from a set of users, the handling network including a sequencing system operable to determine microorganism sequences from sequencing the material; a microbiome characterization system operable to determine microbiome composition data and microbiome functional diversity data based on the microorganism sequences, collect supplementary data associated with the mouth-associated condition for the set of users, and transform the supplementary data and features extracted from the microbiome composition data and the microbiome functional diversity data into a characterization model for the mouth-associated condition; and/or a therapy system operable to promote a treatment to the user based on characterizing the user with the characterization model in relation to the mouth-associated condition.

27 Claims, 12 Drawing Sheets

(56) References Cited

U.S. PATENT DOCUMENTS

| | | |
|---|---|---|
| 9,149,473 B2 | 10/2015 | Ecker et al. |
| 9,433,651 B2 | 9/2016 | Jones et al. |
| 9,506,109 B2 | 11/2016 | Savelkoul et al. |
| 9,663,831 B2 | 5/2017 | Apte et al. |
| 2002/0012926 A1 | 1/2002 | Quake et al. |
| 2003/0190314 A1 | 10/2003 | Campbell et al. |
| 2005/0196785 A1 | 9/2005 | Quake et al. |
| 2006/0089310 A1 | 4/2006 | Goldstein et al. |
| 2007/0134652 A1 | 6/2007 | Slepnev et al. |
| 2007/0259337 A1 | 11/2007 | Hully et al. |
| 2008/0131556 A1 | 6/2008 | De Simone et al. |
| 2010/0172874 A1 | 7/2010 | Turnbaugh et al. |
| 2011/0177976 A1 | 7/2011 | Gordon et al. |
| 2012/0045771 A1 | 2/2012 | Beier et al. |
| 2012/0129794 A1 | 5/2012 | Dowd et al. |
| 2012/0149584 A1 | 6/2012 | Olle et al. |
| 2012/0252775 A1 | 10/2012 | Finegold |
| 2013/0017999 A1 | 1/2013 | Fremont et al. |
| 2013/0045874 A1 | 2/2013 | Ehrlich |
| 2013/0108598 A1 | 5/2013 | Oresic et al. |
| 2013/0184302 A1 | 7/2013 | Bortey et al. |
| 2014/0093478 A1 | 4/2014 | Turnbaugh et al. |
| 2014/0136120 A1 | 5/2014 | Colwell et al. |
| 2014/0179726 A1 | 6/2014 | Bajaj et al. |
| 2014/0315929 A1 | 10/2014 | Chiosis |
| 2014/0341853 A1 | 11/2014 | Hovanky |
| 2015/0050245 A1 | 2/2015 | Herman et al. |
| 2015/0213193 A1 | 7/2015 | Apte et al. |
| 2015/0374761 A1 | 12/2015 | Sadowsky et al. |
| 2016/0032363 A1 | 2/2016 | Stintzi et al. |
| 2016/0040216 A1 | 2/2016 | Akins et al. |
| 2016/0138089 A1 | 5/2016 | Harris et al. |

FOREIGN PATENT DOCUMENTS

| | | |
|---|---|---|
| EP | 2994756 | 3/2016 |
| WO | 050513 | 4/2012 |
| WO | 121298 | 8/2014 |
| WO | 138999 | 9/2014 |
| WO | 144092 | 9/2014 |
| WO | 145958 | 9/2014 |
| WO | 013214 | 1/2015 |
| WO | 085326 | 6/2015 |
| WO | 095241 | 6/2015 |
| WO | 103165 | 7/2015 |
| WO | 112352 | 7/2015 |
| WO | 170979 | 11/2015 |
| WO | 138337 | 9/2016 |
| WO | 172643 | 10/2016 |
| WO | 044902 | 3/2017 |

OTHER PUBLICATIONS

"KEGG: Aminoacyl-tRNA biosynthesis—Reference pathway," Jul. 20, 2013 (Jul. 20, 2013). Retrieved from the internet: <http://web:archive.org/web/20130720015616/http:www.genome.jp/kegg-bin/show_pathway?map=map00970&show_description=show. on Jun. 20, 2016 (Jun. 20.

Carroll et al. "Alterations in composition and diversity of the intestinal microbiota in patients with diarrhea-predominant irritable bowel syndrome," Feb. 20, 2012 (Feb. 29, 2012), vol. 24, pp. 1-19 [Original pp. 5215-5230] entire document.

Cho et al. "The Human Microbiome: at the Interface of Health and Disease," Nature Reviews Genetics, Apr. 1, 2012 (Apr. 1, 2012), vol. 13, pp. 260-270.

Greenblum et al. "Metagenomic Systems and Biology of the Human Gut Microbiome Reveals Topological Shifts Associated with Obesity and Inflammatory Bowel Disease," Proceeding of the National Academy of Sciences, Jan. 10, 2012 (Dec. 19, 2012), vol. 109, Pgs.

Kanehisa et al. "KEGG: Kyoto encyclopedia of genes and genomes," Nucleic Acids Research, Jan. 1, 2000 (Jan. 1, 2000), vol. 28, No. 1, pp. 27-30.

Mak et al. "MetaboLyzer: A Novel Statistical Workflow for Analyzing Post Processed LC/MS Metabolomics Data," Anal Chem, Jan. 7, 2014 (Jan. 7, 2014), vol. 86, pp. 506-513.

Morgan et al. "Dysfunction of the intestinal microbiome in inflammatory bowel disease and treatment," Genome Biol. Apr. 16, 2012 (Apr. 16, 2012), vol. 13(9):R79, pp. 1-18. entire document.

Mutlu et al. "A Compositional Look at the Human Gastrointestinal Microbiome and Immune Activation Parameters in HIV Infected Subjects," PLoS Pathogens, Feb. 20, 2014 (Feb. 20, 2014), vol. 10, pp. 1-18.

Nakayama et al. "Aberrant Structures of Fecal Bacterial Community in Allergic Infants Profiled by 16S rRNA Gene Pyrosequencing," FEMS Immunology & Medical Microbiology, Dec. 1, 2011 (Dec. 1, 2011), vol. 63, pp. 397-406.

Ponnusamy et al. "Microbial community and metabolomic comparison of irritable bowel syndrome faeces," Feb. 17, 2011 (Feb. 17, 2011), vol. 60, pp. 817-827. entire document.

Avila, Maria et al., The Oral Microbiota: Living with a Permanent Guest, DNA and Cell Biology, Nov. 8, 2009, vol. 28, No. 8.

Dewhirst, Floyd et al., The Human Oral Microbiome, Journal of Bacteriology, Oct. 2010, vol. 192, No. 19, pp. 5002-5017.

Evans, Morgan, Prosthetic valve endocarditis due to *Neisseria elongata* subsp. *elongata* in a patient with Klinefelter's syndrome, Journal of Medical Microbiology, Jun. 1, 2007, vol. 56, No. 6, pp. 860-862.

METHOD AND SYSTEM FOR CHARACTERIZING MOUTH-ASSOCIATED CONDITIONS

CROSS-REFERENCE TO RELATED APPLICATIONS

This application is a continuation-in-part of U.S. patent application Ser. No. 15/097,862, filed on 13 Apr. 2016, which claims the benefit of U.S. Provisional Application Ser. No. 62/146,810 filed 13 Apr. 2015, U.S. Provisional Application Ser. No. 62/146,833 filed 13 Apr. 2015, U.S. Provisional Application Ser. No. 62/147,124 filed 14 Apr. 2015, U.S. Provisional Application Ser. No. 62/146,852 filed 13 Apr. 2015, U.S. Provisional Application Ser. No. 62/147,058 filed 14 Apr. 2015, U.S. Provisional Application Ser. No. 62/147,077 filed 14 Apr. 2015, U.S. Provisional Application Ser. No. 62/147,315 filed 14 Apr. 2015, and U.S. Provisional Application Ser. No. 62/147,337 filed 14 Apr. 2015, which are each incorporated in their entirety herein by this reference.

This application additionally claims the benefit of U.S. Provisional Application Ser. No. 62/304,642 filed 7 Mar. 2016, and U.S. Provisional Application Ser. No. 62/304,645 filed 7 Mar. 2016, which are each incorporated in their entirety by this reference.

TECHNICAL FIELD

This invention relates generally to the field of microbiology and more specifically to a new and useful method and system for characterizing mouth-associated conditions in the field of microbiology.

BACKGROUND

A microbiome is an ecological community of commensal, symbiotic, and pathogenic microorganisms that are associated with an organism. The human microbiome includes over 10 times more microbial cells than human cells, but characterization of the human microbiome is still in nascent stages due to limitations in sample processing techniques, genetic analysis techniques, and resources for processing large amounts of data. Nonetheless, the microbiome is suspected to play at least a partial role in a number of health/disease-related states (e.g., preparation for childbirth, diabetes, auto-immune disorders, gastrointestinal disorders, rheumatoid disorders, neurological disorders, etc.). Given the profound implications of the microbiome in affecting a subject's health, efforts related to the characterization of the microbiome, the generation of insights from the characterization, and the generation of therapeutics configured to rectify states of dysbiosis should be pursued. Current methods and systems for analyzing the microbiomes of humans and providing therapeutic measures based on gained insights have, however, left many questions unanswered. In particular, methods for characterizing certain health conditions and therapies (e.g., probiotic therapies) tailored to specific subjects based upon microbiome composition and/or functional features have not been viable due to limitations in current technologies.

As such, there is a need in the field of microbiology for a new and useful method and system for characterizing health conditions in an individualized and population-wide manner. This invention creates such a new and useful method and system.

DESCRIPTION OF THE EMBODIMENTS

The following description of the embodiments of the invention is not intended to limit the invention to these embodiments, but rather to enable any person skilled in the art to make and use this invention.

1. Overview.

Figure 2:
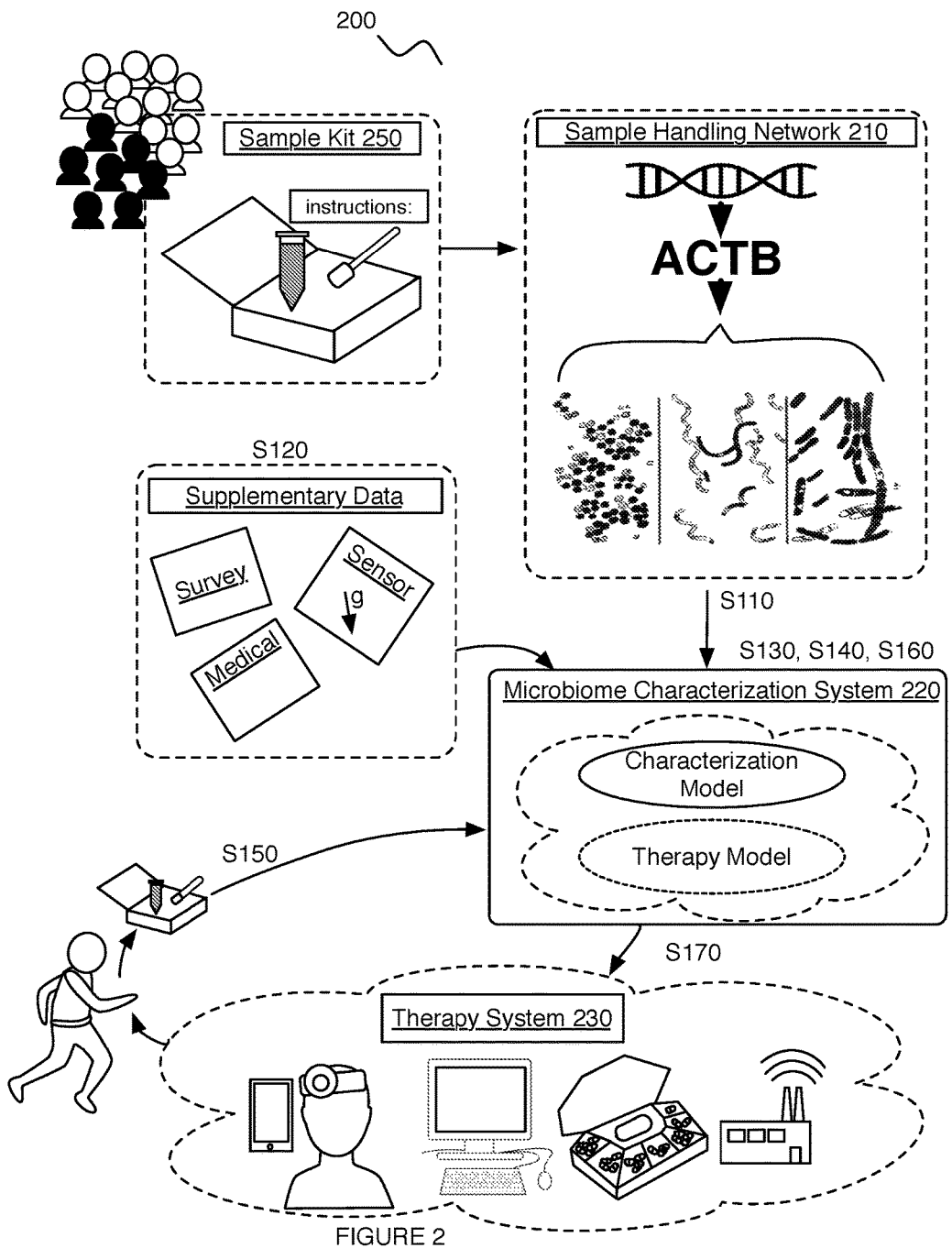
FIG. 2 depicts variations of embodiments of a system and method for microbiome characterization.

As shown in FIG. 2, an embodiment of a system 200 for characterizing (e.g., evaluating) a mouth-associated condition in relation to a user (e.g., a human subject, an animal subject, etc.) can include one or more of: a handling network (e.g., sample handling network) 210 operable to collect containers including material (e.g., biological samples including microorganism nucleic acid material, etc.) from a set of users (e.g., a population of users), the handling network including a sequencing system operable to determine microorganism sequences from sequencing the material; a microbiome characterization system 220 operable to determine microbiome composition data and microbiome functional diversity data based on the microorganism sequences, collect supplementary data associated with the mouth-associated condition for the set of users, and transform the supplementary data and features extracted from the microbiome composition data and the microbiome functional diversity data into a characterization model for the mouth-associated condition; and/or a therapy system (e.g., treatment system) 230 operable to promote a treatment to the user based on characterizing the user with the characterization model in relation to the mouth-associated condition.

The system 200 and method 100 can function to generate models that can be used to characterize and/or diagnose subjects according to at least one of their microbiome composition and functional features (e.g., as a clinical diagnostic, as a companion diagnostic, etc.); provide therapeutic measures (e.g., probiotic-based therapeutic measures, phage-based therapeutic measures, small-molecule-based therapeutic measures, clinical measures, etc.) to subjects based upon microbiome analysis for a population of subjects; and/or perform any suitable function. The system 200 and method 100 can preferably generate characterizations and therapies for mouth-associated conditions, which can include any one or more of: gingivitis, halitosis, periodontal disease, dental caries, cavities, tooth loss, oral cancer, canker sores, oral herpes, herpangina, thrush, oral gonorrhea, hand-foot-and-mouth disease, fungal infections, bacterial infections, viral infections, oro-dental trauma, noma, cleft lip, xerostomia, candidiasis, denture stomatitis, plaque, tartar, and/or any other suitable mouth-associated condition (e.g., symptoms, causes, diseases, disorders, etc.); however, characterizations and/or therapies can be tailored to any suitable user condition. The system 200 and/or components of the system 200 preferably implement the method 100 and/or portions of the method 100, but any suitable components can partially and/or fully implement any number of instance of any portions of the method 100 (e.g., in serial, in parallel, etc.).

2. Benefits

Microbiome analysis can enable accurate and efficient characterization of mouth-associated conditions caused by and/or otherwise associated with microorganisms. The technology can overcome several challenges faced by conventional approaches in characterizing mouth-associated conditions. First, conventional approaches to characterizing mouth-associated conditions can require patients to visit a care provider (e.g., dentist, physician, etc.), who performs a physical inspection of the mouth. Second, conventional genetic sequencing and analysis technologies for human genome sequencing can be incompatible and/or inefficient when applied to the microbiome (e.g., where the human microbiome can include over 10 times more microbial cells than human cells; where optimal sample processing techniques can differ; where sequence reference databases can differ; where microbiome characterization can include accounting for the different compositions and functional diversity of the microbiome across populations; etc.). Third, the onset of sequencing technologies (e.g., next-generation sequencing) has given rise to technological issues (e.g., data processing issues, information display issues, microbiome analysis issues, therapy prediction issues, etc.) that would not exist but for the unprecedented advances in speed and data generation associated with sequencing nucleic acid material. Examples of the system 200 and the method 100 can confer technologically-rooted solutions to at least the challenges described above.

First, the technology can confer improvements in computer-related technology (e.g., artificial intelligence, machine learning, etc.) by facilitating computer performance of functions not previously performable. For example, the technology can computationally generate microbiome characterizations and recommended therapies for mouth-associated conditions, based on microbiome sequence datasets and microorganism reference sequence databases (e.g., Genome Reference Consortium) that are recently viable due to advances in sample processing techniques and sequencing technology.

Second, the technology can confer improvements in processing speed and microbiome characterization accuracy. The technology can generate and apply mouth-associated feature-selection rules to select an optimized subset of features (e.g., microbiome composition features, microbiome functional diversity features, etc.) out of a vast potential pool of features (e.g., extractable from the plethora of microbiome data) for generating and applying characterization models and/or therapy models. The potential size of microbiomes (e.g., human microbiomes, animal microbiomes, etc.) can translate into a plethora of data, giving rise to questions of how to process and analyze the vast array of data to generate actionable microbiome insights in relation to mouth-associated conditions. However, the mouth-associated feature-selection rules and associated technology can enable shorter training and execution times (e.g., for predictive machine learning models), model simplification facilitating efficient interpretation of results, reduction in overfitting, and other suitable improvements to facilitate rapid determination of characterizations and/or therapies.

Third, the technology can transform entities (e.g., users, biological samples, therapy systems including medical devices, etc.) into different states or things. For example, the system 200 and/or method 100 can identify therapies to promote to a patient to modify microbiome composition and/or function to prevent and/or ameliorate mouth-associated conditions, thereby transforming the microbiome and/or health of the patient. In another example, the technology can transform biological samples (e.g., through fragmentation, multiplex amplification, sequencing, etc.) received by patients into microbiome datasets usable in generating characterization models and/or therapy models. In another example, the technology can control therapy systems to promote therapies (e.g., by generating control instructions for the therapy system to execute), thereby transforming the therapy system.

Fourth, the technology can amount to an inventive distribution of functionality across a network including a sample handling network, microbiome characterization system, and a plurality of users, where the sample handling network can handle simultaneous processing of biological samples (e.g., in a multiplex manner) from the plurality of users, which can be leveraged by the microbiome characterization system in generating user-personalized characterizations and/or therapies (e.g., customized to the user's microbiome, medical history, demographics, behaviors, preferences, etc.) for mouth-associated conditions. The technology can, however, alone and in combination, provide any other suitable benefit(s) in the context of using non-generalized computer systems for characterizing a microbiome and/or promoting a relevant therapy.

3. System.

The handling network 210 of the system 200 can function to receive and process (e.g., fragment, amplify, sequence, etc.) biological samples to transform microorganism nucleic acids of the biological samples into genetic sequences that can be subsequently aligned and analyzed to generate characterizations of and therapies for mouth-associated conditions. The handling network 210 can additionally or alternatively function to provide sample kits 250 (e.g., including sample containers, instructions for collecting mouth samples, etc.) to a plurality of users (e.g., in response to a purchase order for a sample kit 250), such as through a mail delivery system. The handling network 210 can additionally or alternatively include a library preparation system operable to automatically prepare biological samples (e.g., fragment and amplify using primers compatible with genetic targets associated with the mouth-associated condition) in a multiplex manner to be sequenced by a sequencing system; and/or any suitable components. However, the handling network 210 and associated components can be configured in any suitable manner.

The microbiome characterization system 220 of the system 200 can function to determine and analyze microbiome datasets based on processed biological samples (e.g., microorganism genetic sequences; alignments to reference sequences; etc.) to generate and/or apply a characterization model for characterizing one or more mouth-associated conditions. The microbiome characterization system 220 can additionally or alternatively function to generate and/or apply a therapy model for identifying a therapy used to treat a mouth-associated condition; to promote the therapy (e.g., acting as a therapy system 230 to generate and/or output a therapy recommendation to a subject at a user device); process supplementary data (e.g., in generating and/or applying characterization models and/or therapy models); and/or perform any suitable function. In a variation, the microbiome characterization system 220 can obtain and/or apply computer-implemented rules (e.g., feature selection rules; model generation rules; user preference rules, and/or any other suitable rules). For example, the microbiome characterization system 220 can apply mouth-associated feature-selection rules to facilitate decreased processing time in generating a model (e.g., transforming supplementary data and features into the characterization model, etc.). The microbiome characterization system 220 preferably includes a remote computing system, but can additionally or alternatively include any suitable processing systems. However, the microbiome characterization system 220 can be configured in any suitable manner.

The therapy system 230 of the system 200 functions to promote one or more therapies to a user (e.g., subject; care provider who administer the therapy; etc.) for treating a mouth-associated condition (e.g., reducing the risk of a mouth-associated infection, etc.). The therapy system 230 can include any one or more of: a communications system (e.g., to communicate therapy recommendations to a user device and/or care provider device; to enable telemedicine between a care provider and a subject in relation to a mouth-associated condition; etc.), an application executable on a user device (e.g., an oral hygiene application for recommending proper oral hygiene therapies operable to modify microbiome composition in the mouth; etc.), oral treatments (e.g., oral rinses, antiseptic chips, antibiotic gels, antibiotic microspheres, enzyme suppressants, medications such as oral antibiotics, etc.), a medical device (e.g., teeth trays; oral strips; gum cleaning devices; teeth cleaning devices; automatic medication dispensers; a biological sampling device, such as for collecting gingival samples; surgical systems such as for flap surgery or bone and tissue grafts; etc.), a user device (e.g., biometric sensors), and/or any other suitable component. One or more therapy systems 230 are preferably controllable by the microbiome characterization system 220. For example, the microbiome characterization system 220 can generate control instructions and/or notifications to transmit to the therapy system 230 for activating and/or otherwise operating the therapy system in promoting the therapy. In another example, the microbiome characterization system 220 can update and/or otherwise modify an application and/or other software of a device (e.g., user smartphone) to promote a therapy (e.g., promoting, at a to-do list application, lifestyle changes such as flossing for modifying microbiome functional diversity in the mouth to reduce the risk of mouth-associated conditions, etc.). However, the therapy system 230 can be configured in any other manner.

Figure 9:
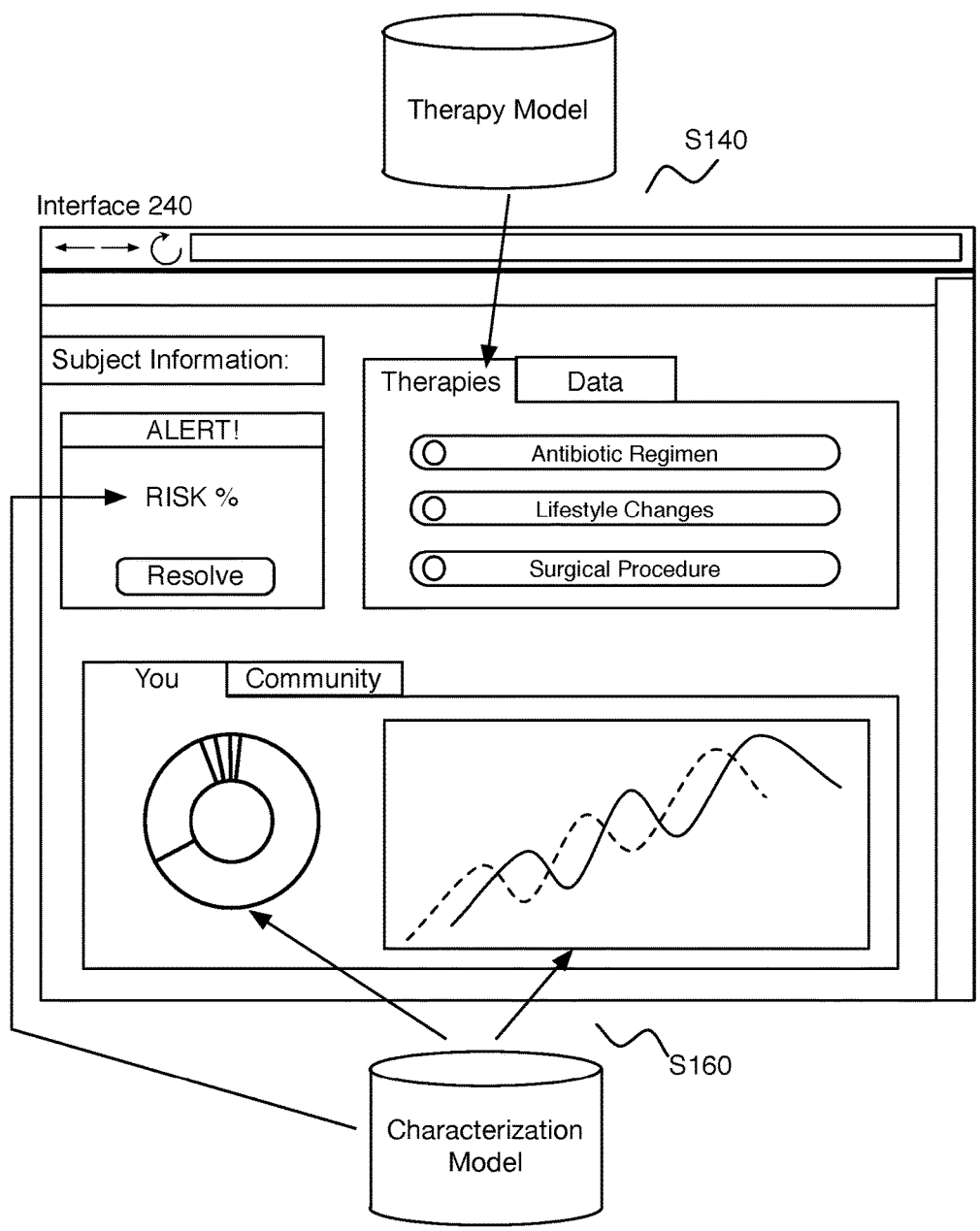
FIG. 9 depicts a variation of an interface for providing mouth-associated condition information in an embodiment of a method for microbiome characterization.
Figure 11:
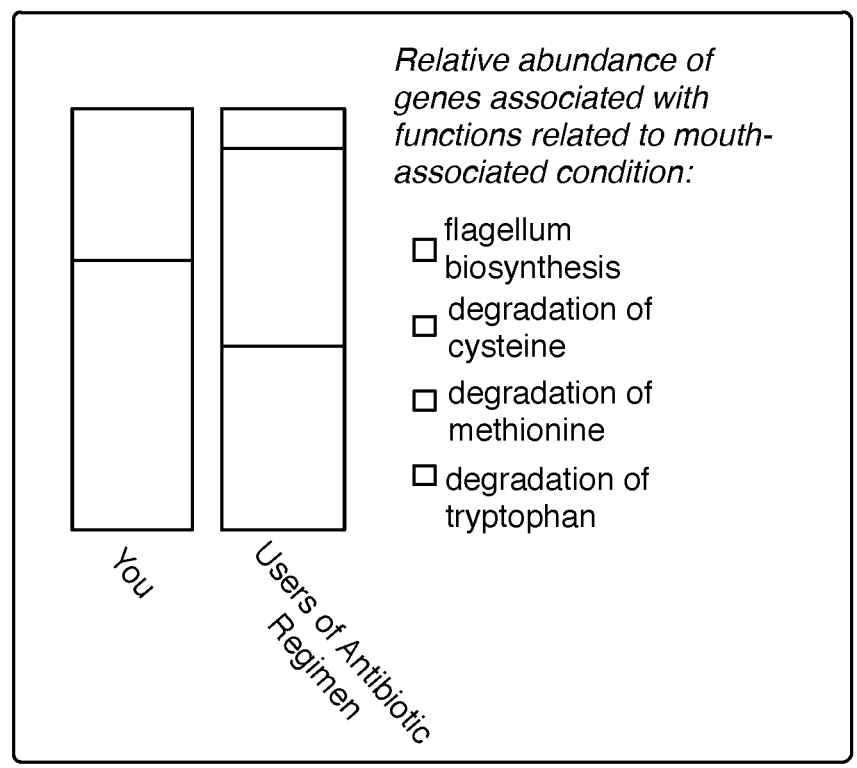
FIG. 11 depicts a variation of notification provision in an embodiment of a method for microbiome characterization.

As shown in FIG. 9, the system 200 can additionally or alternatively include an interface 240 that can function to improve presentation of mouth-associated condition information (e.g., characterizations; therapy recommendations; comparisons to other users; etc.). In examples, the interface 240 can present mouth-associated condition information including a microbiome composition (e.g., taxonomic groups such as *Spirochaetes* and *Oribacterium*), functional diversity (e.g., relative abundance of genes associated with flagellum biosynthesis, as shown in FIG. 11, etc.), risk of infection (e.g., of a gingivitis-associated condition and a halitosis-associated condition) for the user, such as relative to a user group sharing a demographic characteristic (e.g., dental patients, smokers, exercisers, users on different dietary regimens, consumers of probiotics, antibiotic users, groups undergoing particular therapies, etc.). However, the interface 240 can be configured in any suitable manner.

While the components of the system 200 are generally described as distinct components, they can be physically and/or logically integrated in any manner. For example, a smartphone application can implement both the microbiome characterization system 220 (e.g., apply a characterization model to generate a characterization of mouth-associated conditions) and the therapy system 230 (e.g., schedule daily events at a calendar application of the smartphone to notify the user to take probiotic therapies in response to generating the characterization). However, the functionality of the system 200 can be distributed in any suitable manner amongst any suitable system components. Additionally or alternatively, the system 200 and/or method 100 can include any suitable components and/or functions analogous to (e.g., applied in the context of mouth-associated conditions) those described in U.S. application Ser. No. 15/374,890 filed 9 Dec. 2016, U.S. application Ser. No. 14/593,424 filed 9 Jan. 2015, U.S. application Ser. No. 15/198,818 filed 30 Jun. 2016, U.S. application Ser. No. 15/098,027 filed 13 Apr. 2016, U.S. application Ser. No. 15/098,248 filed 13 Apr. 2016, U.S. application Ser. No. 15/098,236 filed 13 Apr. 2016, Ser. No. 15/098,222 filed 13 Apr. 2016, U.S. application Ser. No. 15/098,204 filed 13 Apr. 2016, U.S. application Ser. No. 15/098,174 filed 13 Apr. 2016, U.S. application Ser. No. 15/098,110 filed 13 Apr. 2016, U.S. application Ser. No. 15/098,081 filed 13 Apr. 2016, U.S. application Ser. No. 15/098,153 filed 13 Apr. 2016, U.S. application Ser. No. 15/228,890 filed 4 Aug. 2016, and U.S. application Ser. No. 15/240,919 filed 18 Aug. 2016, which are each hereby incorporated in their entirety by this reference. However, the components of the system 200 can be configured in any suitable manner.

4. Method.

Figure 1A:
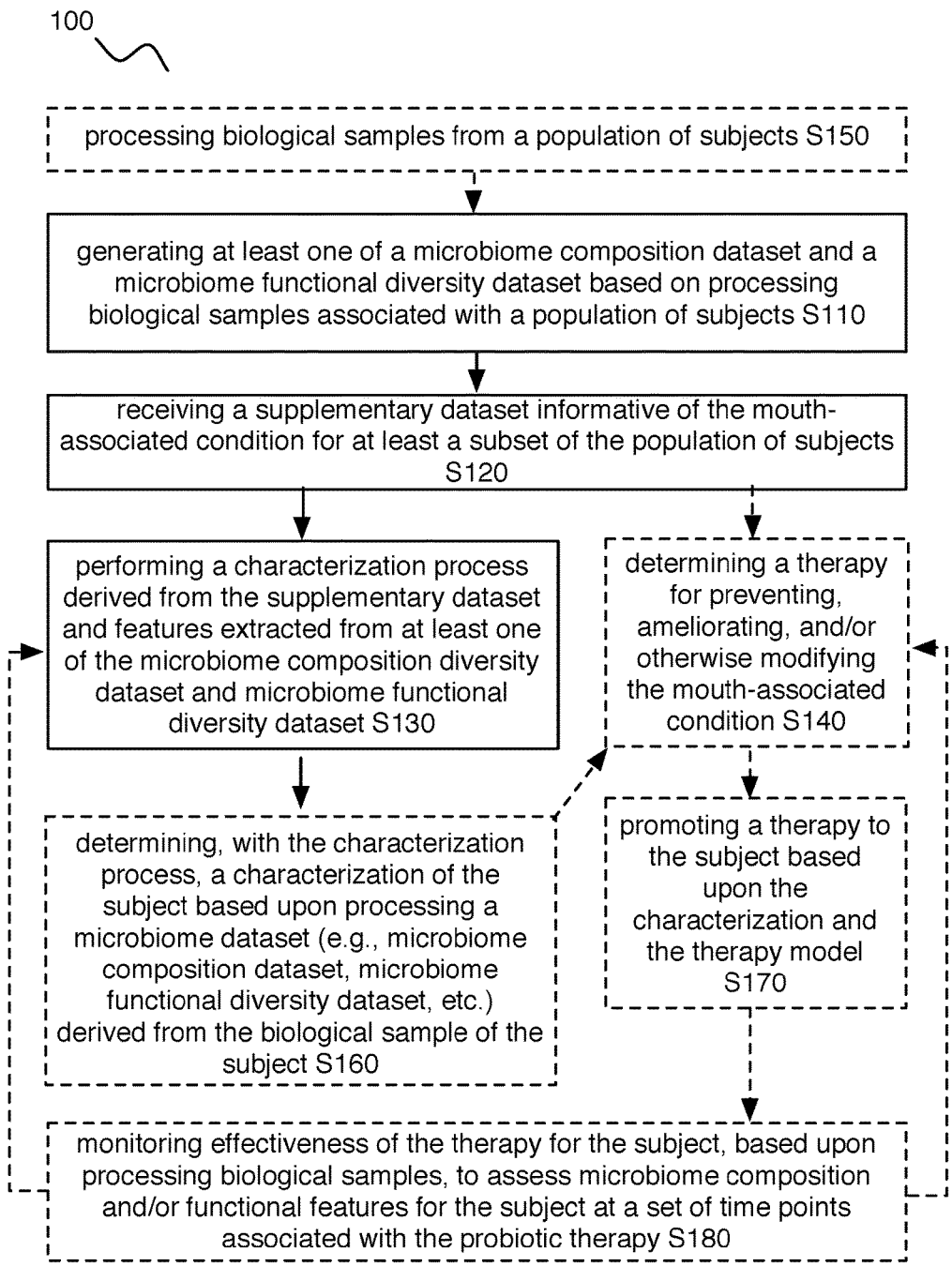
FIGS. 1A-1B are flowchart representations of variations of an embodiment of a method for microbiome characterization.
Figure 1B:
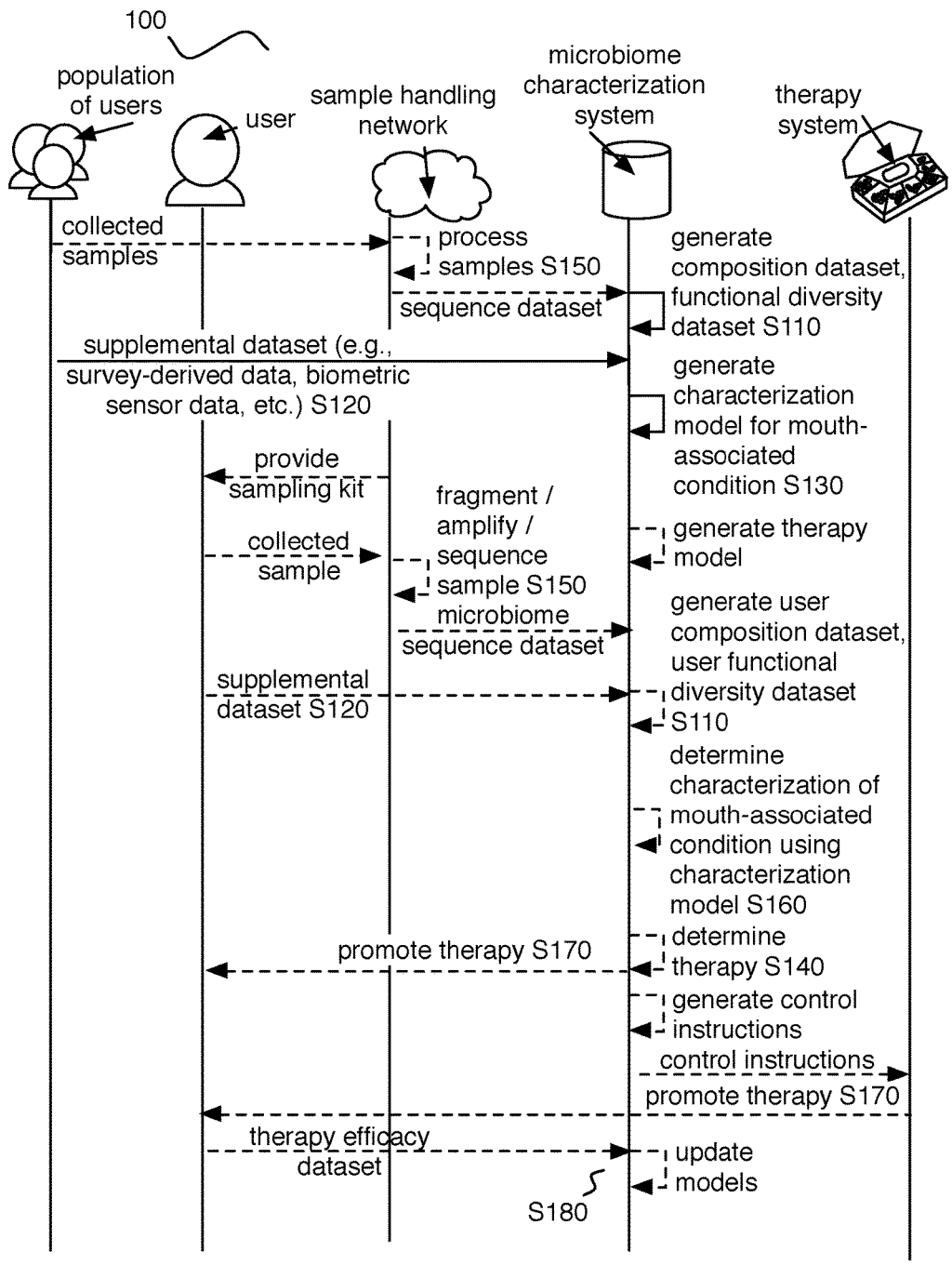

As shown in FIGS. 1A-1B, an embodiment of a method 100 for characterizing a mouth-associated condition in relation to a user can include one or more of: generating at least one of a microbiome composition dataset and a microbiome functional diversity dataset based on biological samples (e.g., microorganism genetic sequences derived from the samples) associated with a set of users S110; processing a supplementary dataset informative of the mouth-associated condition for the set of users S120; and performing a characterization process for one or mouth-associated conditions, the characterization process derived from the supplementary dataset and features extracted from at least one of the microbiome composition dataset and microbiome functional diversity dataset S130. The method 100 can additionally or alternatively include one or more of: determining a therapy for preventing, ameliorating, and/or otherwise modifying a mouth-associated condition S140; processing a biological sample from a subject S150; determining, with the characterization process, a characterization of the subject based upon processing a microbiome dataset (e.g., microbiome composition dataset, microbiome functional diversity dataset, etc.) derived from the biological sample of the subject S160; promoting a therapy to the subject based upon a therapy model S170; monitoring effectiveness of the therapy for the subject, based upon processing biological samples, to assess microbiome composition and/or functional features associated with the therapy for the subject over time S180; and/or any other suitable operations.

4.1 Method—Processing Datasets.

Figure 10:
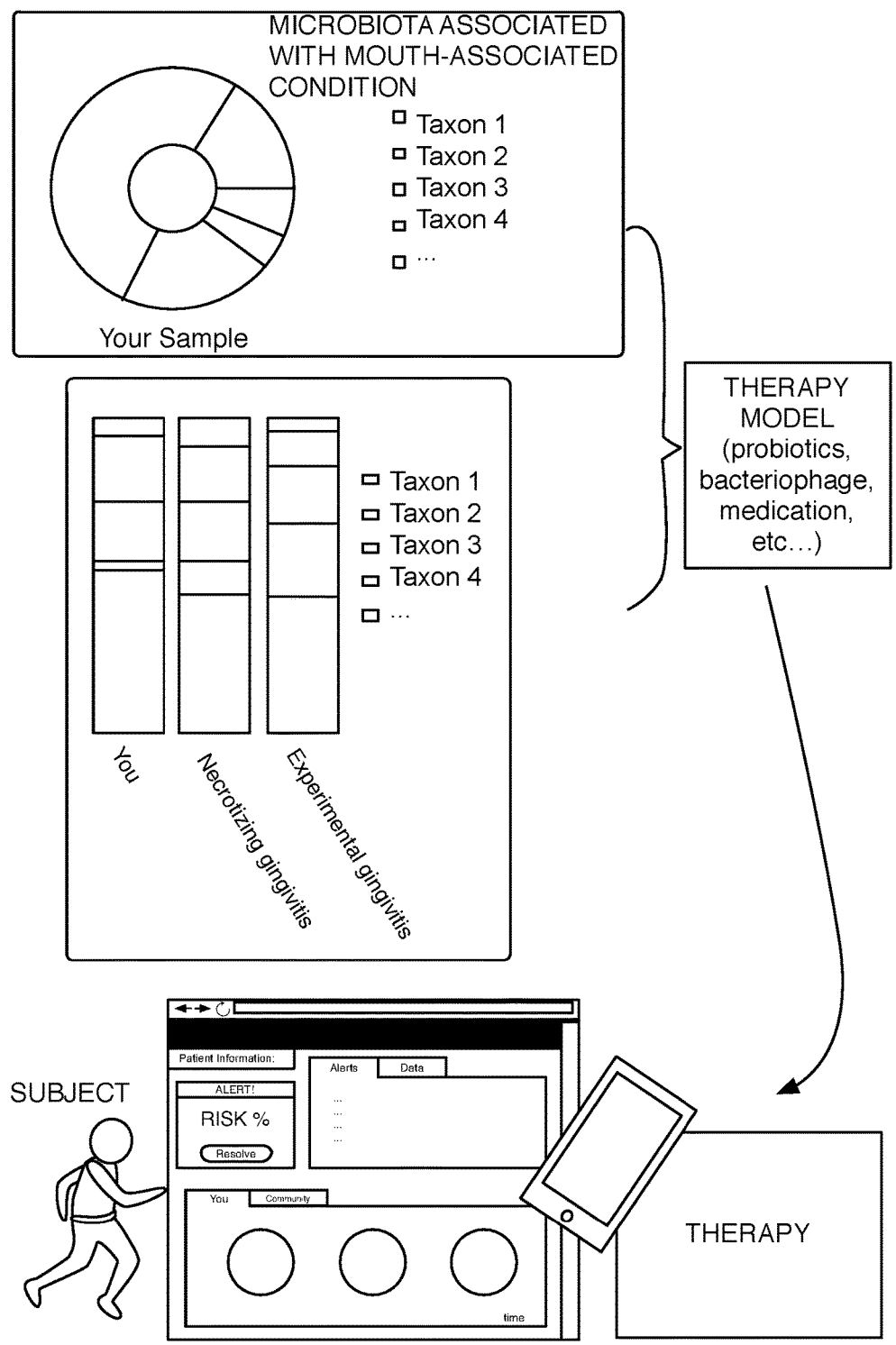
FIG. 10 depicts variations of notification provision in an embodiment of a method for microbiome characterization.

Block S110 recites: generating at least one of a microbiome composition dataset and a microbiome functional diversity dataset based on biological samples associated with a set of users. Block S110 functions to process each of an aggregate set of biological samples, in order to determine compositional and/or functional aspects associated with the microbiome of each of a population of subjects. As shown in FIG. 10, compositional and functional aspects can include compositional aspects at the microorganism level, including parameters related to distribution of microorganisms across different groups of kingdoms, phyla, classes, orders, families, genera, species, subspecies, strains, and/or any other suitable infraspecies taxon (e.g., as measured in total abundance of each group, relative abundance of each group, total number of groups represented, etc.). Compositional and functional aspects can also be represented in terms of operational taxonomic units (OTUs). Compositional and functional aspects can additionally or alternatively include compositional aspects at the genetic level (e.g., regions determined by multilocus sequence typing, 16S sequences, 18S sequences, ITS sequences, other genetic markers, other phylogenetic markers, etc.). Compositional and functional aspects can include the presence or absence or the quantity of genes associated with specific functions (e.g. enzyme activities, transport functions, immune activities, etc.). Outputs of Block S110 can thus be used to provide features of interest for the characterization process of Block S130 and/or the therapy process of Block S140, where the features can be microorganism-based (e.g., presence of a genus of bacteria), genetic-based (e.g., based upon representation of specific genetic regions and/or sequences) and/or functional-based (e.g., presence of a specific catalytic activity), and/or otherwise configured. In one variation, Block S110 can include assessment and/or processing based upon any suitable phylogenetic markers derived from bacteria and/or archaea in relation to any suitable gene families.

In variations, sample processing in Block S110 can include any one or more of: lysing a biological sample, disrupting membranes in cells of a biological sample, separation of undesired elements (e.g., RNA, proteins) from the biological sample, purification of nucleic acids (e.g., DNA) in a biological sample, amplification (e.g., with a library preparation system) of nucleic acids from the biological sample, further purification of amplified nucleic acids of the biological sample, and sequencing of amplified nucleic acids of the biological sample, and/or other suitable sample processing operations. In variations of Block S110, lysing a biological sample and/or disrupting membranes in cells of a biological sample can include any approaches described in relation to U.S. application Ser. No. 15/374,890 filed 9 Dec. 2016, which is incorporated in its entirety by this reference.

In variations of Block S110, amplification of purified nucleic acids preferably includes one or more of: polymerase chain reaction (PCR)-based techniques (e.g., solid-phase PCR, RT-PCR, qPCR, multiplex PCR, touchdown PCR, nano PCR, nested PCR, hot start PCR, etc.), helicase-dependent amplification (HDA), loop mediated isothermal amplification (LAMP), self-sustained sequence replication (3SR), nucleic acid sequence based amplification (NASBA), strand displacement amplification (SDA), rolling circle amplification (RCA), ligase chain reaction (LCR), and any other suitable amplification technique. In amplification of purified nucleic acids, the primers used are preferably selected to prevent or minimize amplification bias, as well as configured to amplify nucleic acid regions/sequences (e.g., of the 16S region, the 18S region, the ITS region, etc.) that are informative taxonomically, phylogenetically, for diagnostics, for formulations (e.g., for probiotic formulations), and/or for any other suitable purpose. Thus, universal primers (e.g., a F27-R338 primer set for 16S RNA, a F515-R806 primer set for 16S RNA, etc.) configured to avoid amplification bias can be used in amplification. Primers used in variations of Block S110 can additionally or alternatively include incorporated barcode sequences specific to each biological sample, which can facilitate identification of biological samples post-amplification. Selected primers can additionally or alternatively be associated with a mouth-associated condition and/or microbiome composition features, functional features, supplementary features, and/or other features associated with the mouth-associated condition). For example, the primers can be complementary to genetic targets associated with the features (e.g., genetic sequences from which relative abundance features are derived; genes associated with flagellum biosynthesis; etc.). Primers used in variations of Block S110 can additionally or alternatively include adaptor regions configured to cooperate with sequencing techniques involving complementary adaptors (e.g., Illumina Sequencing). Additionally or alternatively, Block S110 can implement any other step configured to facilitate processing (e.g., using a Nextera kit).

In variations of Block S110, sequencing of purified nucleic acids can include methods involving targeted amplicon sequencing and/or metagenomic sequencing, implementing techniques including one or more of: sequencing-by-synthesis techniques (e.g., Illumina sequencing), capillary sequencing techniques (e.g., Sanger sequencing), pyrosequencing techniques, and nanopore sequencing techniques (e.g., using an Oxford Nanopore technique).

In a specific example of Block S110, amplification and sequencing of nucleic acids from biological samples of the set of biological samples includes: solid-phase PCR involving bridge amplification of DNA fragments of the biological samples on a substrate with oligo adapters, where amplification involves primers having a forward index sequence (e.g., corresponding to an Illumina forward index for MiSeq/NextSeq/HiSeq platforms), a forward barcode sequence, a transposase sequence (e.g., corresponding to a transposase binding site for MiSeq/NextSeq/HiSeq platforms), a linker (e.g., a zero, one, or two-base fragment configured to reduce homogeneity and improve sequence results), an additional random base, a sequence for targeting a specific target region (e.g., 16S region, 18S region, ITS region), a reverse index sequence (e.g., corresponding to an Illumina reverse index for MiSeq/HiSeq platforms), and a reverse barcode sequence. In the specific example, sequencing includes Illumina sequencing (e.g., with a HiSeq platform, with a MiSeq platform, with a NextSeq platform, etc.) using a sequencing-by-synthesis technique.

Some variations of sample processing in Block S110 can include further purification of amplified nucleic acids (e.g., PCR products) prior to sequencing, which functions to remove excess amplification elements (e.g., primers, dNTPs, enzymes, salts, etc.). In examples, additional purification can be facilitated using any one or more of: purification kits, buffers, alcohols, pH indicators, chaotropic salts, nucleic acid binding filters, centrifugation, and any other suitable purification technique.

In variations, computational processing in Block S110 can include any one or more of: identification of microbiome-derived sequences (e.g., as opposed to subject sequences and contaminants), alignment and mapping of microbiome-derived sequences (e.g., alignment of fragmented sequences using one or more of single-ended alignment, ungapped alignment, gapped alignment, pairing), and generating features derived from compositional and/or functional aspects of the microbiome associated with a biological sample.

In Block S110, identification of microbiome-derived sequences can include mapping of sequence data from sample processing to a subject reference genome (e.g., provided by the Genome Reference Consortium), in order to remove subject genome-derived sequences. In an example, Block S110 can include determining alignments between microorganism nucleic acid sequences and reference sequences associated with the mouth-associated condition (e.g., microbiome biomarkers associated with the mouth-associated conditions, such as biomarkers indicative of a presence and/or abundance of genetic sequences representative of *Spirochaetes*, etc.) where generating the microbiome composition dataset and the microbiome functional diversity dataset is based on the alignments. However, mapping sequence data can be performed in any suitable manner, such as analogous to U.S. application Ser. No. 15/374,890 filed 9 Dec. 2016, which is incorporated in its entirety by this reference.

In Block S110, upon identification of represented groups of microorganisms of the microbiome associated with a biological sample, generating features derived from compositional and functional aspects of the microbiome associated with a biological sample can be performed. In one variation, generating features can include generating features based upon multilocus sequence typing (MSLT), in order to identify markers useful for characterization in subsequent blocks of the method 100. Additionally or alternatively, generating features can include generating features that describe the presence or absence of certain taxonomic groups of microorganisms, and/or ratios between exhibited taxonomic groups of microorganisms. Additionally or alternatively, generating features can include generating features describing one or more of: quantities of represented taxonomic groups, networks of represented taxonomic groups, correlations in representation of different taxonomic groups, interactions between different taxonomic groups, products produced by different taxonomic groups, interactions between products produced by different taxonomic groups, ratios between dead and alive microorganisms (e.g., for different represented taxonomic groups, based upon analysis of RNAs), phylogenetic distance (e.g., in terms of Kantorovich-Rubinstein distances, Wasserstein distances etc.), any other suitable taxonomic group-related feature(s), any other suitable genetic or functional feature(s).

In relation to Block S110, additionally or alternatively, generating features can include generating features describing relative abundance of different microorganism groups, for instance, using a sparCC approach, using Genome Relative Abundance and Average size (GAAS) approach and/or using a Genome Relative Abundance using Mixture Model theory (GRAMMy) approach that uses sequence-similarity data to perform a maximum likelihood estimation of the relative abundance of one or more groups of microorganisms. Additionally or alternatively, generating features can include generating statistical measures of taxonomic variation, as derived from abundance metrics. Additionally or alternatively, generating features can include generating features derived from relative abundance factors (e.g., in relation to changes in abundance of a taxon, which affects abundance of other taxa). Additionally or alternatively, generating features can include generation of qualitative features describing presence of one or more taxonomic groups, in isolation and/or in combination. Additionally or alternatively, generating features can include generation of features related to genetic markers (e.g., representative 16S, 18S, and/or ITS sequences) characterizing microorganisms of the microbiome associated with a biological sample. Additionally or alternatively, generating features can include generation of features related to functional associations of specific genes and/or organisms having the specific genes. Additionally or alternatively, generating features can include generation of features related to pathogenicity of a taxon and/or products attributed to a taxon. Block S120 can, however, include generation of any other suitable feature(s) derived from sequencing and mapping of nucleic acids of a biological sample. For instance, the feature(s) can be combinatory (e.g. involving pairs, triplets), correlative (e.g., related to correlations between different features), and/or related to changes in features (e.g., temporal changes, changes across sample sites, etc., spatial changes, etc.). However, Block S110 can be performed in any suitable manner.

Block S120 recites: processing a supplementary dataset informative of the mouth-associated condition for the set of users. Block S120 functions to acquire additional data associated with one or more subjects of the set of subjects, which can be used to train and/or validate the characterization process generated in Block S130. In Block S120, the supplementary dataset preferably includes survey-derived data, but can additionally or alternatively include any one or more of: contextual data derived from sensors, medical data (e.g., current and historical medical data), and any other suitable type of data. In variations of Block S120 including reception of survey-derived data, the survey-derived data preferably provides physiological, demographic, and behavioral information in association with a subject. However, types of supplementary data and manners of collecting supplementary data can be analogous to that described in U.S. application Ser. No. 15/374,890 filed 9 Dec. 2016, which is incorporated in its entirety by this reference, but processing supplementary datasets can be otherwise performed.

4.2 Method—Performing a Characterization Process.

Block S130 recites: performing a characterization process derived from the supplementary dataset and features extracted from at least one of the microbiome composition diversity dataset and microbiome functional diversity dataset. Block S130 can additionally or alternatively include generating features S132, generating a characterization model S134, and/or any other suitable operations. Block S130 functions to identify features and/or feature combinations that can be used to characterize subjects or groups based upon their microbiome composition and/or functional features. As such, the characterization process can be used as a diagnostic tool that can characterize a subject (e.g., in terms of behavioral traits, in terms of medical conditions, in terms of demographic traits, etc.) based upon their microbiome composition and/or functional features, in relation to one or more of their health condition states, behavioral traits, medical conditions, demographic traits, and any other suitable traits. Such characterization can then be used to suggest or provide personalized therapies by way of the therapy model of Block S140.

In performing the characterization process, Block S130 can use computational methods (e.g., statistical methods, machine learning methods, artificial intelligence methods, bioinformatics methods, etc.) to characterize a subject as exhibiting features characteristic of a group of subjects with a health condition. However, the characterization process can be performed in any suitable manner.

In variations of Block S130, performing a characterization process can include generating one or more characterizations of mouth-associated conditions (e.g., a gingivitis-associated condition, a halitosis-associated condition, etc.). In some examples, the characterization process of Block S130 can facilitate identification of which microorganism population(s) (e.g., taxonomic groups, microbiome composition features, etc.) are upregulated or downregulated in relation to mouth-associated conditions, and/or which microbiome functional aspects (e.g., in relation to Clusters of Orthologous Groups/Kyoto Encyclopedia of Genes and Genomes pathways, microbiome functional diversity features, etc.) are upregulated or downregulated in relation to mouth-associated conditions. In specific examples, the characterization processes of Block S130 can include characterizing species of a *Spirochaetes* (e.g., *Treponema denticola, T. macrodentium, T. microdentium, T. oralis*, etc.) present in a biological sample; and characterizing, at the species level, relationship(s) between species of *Spirochaetes* and microorganism population and/or functional aspects in relation to one or more mouth-associated conditions. Additionally or alternatively, Block S130 can include performing the characterization process at any suitable taxonomic level (e.g., kingdom, phylum, class, order, family, genus, species, etc.), at the strain level, and/or at any suitable level of granularity.

In another variation, characterizing a mouth-associated condition in Block S130 can include generating a diagnostic analysis of a mouth-associated condition (e.g., estimating a risk of being inflicted by the mouth-associated condition, diagnosing the presence of the mouth-associated condition, etc.) and/or associated complications, such as based on at least one of microbiome composition features, microbiome functional diversity features, and/or other suitable features. In another variation of Block S130, characterizing a mouth-associated condition can be based on one or more supplementary datasets. For example, the set of feature-selection rules can correlate a mouth-associated condition to one or more biometric features derived from biometric sensor data informative of a mouth-associated condition (e.g., optical data of the mouth and/or other body regions; breath data; blood data; temperature data; user behavior data; temperature data; cardiovascular data; stool data; etc.) indicating the presence of symptoms associated with one or more of: gums (e.g., redness; bleeding; swelling; tissue recession; root surface exposure; etc.); teeth (e.g., pain; loss; etc.); breath; and/or any portion of mouth or body. In another example, performing a characterization process can be based on antibiotic regimen data, probiotic regimen data, and/or other suitable therapy data associated with a population of users, where particular regimens can aid in illuminating microbiome compositions and/or functional diversity correlated with mouth-associated conditions. However, performing a characterization process in relation to a mouth-associated condition can be performed in any suitable manner.

In another variation, characterizing a mouth-associated condition in Block S130 can include predicting indices indicative of plaque and debris (e.g., plaque index with scores of 0 to 3 based on accumulation of deposits within gingival pockets, etc.), calculus assessment (e.g., calculus surface index with scores of 1 to 4 based on quantity of gingival calculus, etc.), gingival disease (e.g., gingival index with scores of 0 to 3 based on severity of gingival inflammation, etc.), periodontal disease (e.g., periodontal disease index with scores of 0 to 3 based on gingival components, plaque components, and calculus components, etc.), dental fluorosis (e.g., Dean's Fluorosis Index, Simplified Fluoride Mottling Index, etc.), and/or any other suitable indices. In another variation, characterizing a mouth-associated condition can be based on supplementary data including one or more of the above-described indices. However, any suitable indices can be used in any suitable manner.

Block S130 can additionally or alternatively include Block S132: generating features. Block S132 functions to generate one or more features for use in the characterization process (e.g., generating a characterization model). Features can include any one or more of: microbiome composition features (e.g., absolute and/or relative abundance of taxonomic groups in a user's microbiome), microbiome functional diversity features, and/or other suitable features. Microbiome functional diversity features can include any one or more of: Kyoto Encyclopedia of Genes and Genomes (KEGG) functional features (e.g., KEGG features associated with flagellum biosynthesis, etc.), Clusters of Orthologous Groups (COG) of proteins features, genomic functional features, functional features associated with and/or specific to a taxonomic group, chemical functional features (e.g., cysteine metabolism, etc.), systemic functional features (e.g., systemic immune function; functions associated with systemic diseases; etc.), and/or any suitable functional features.

Regarding Block S132, determining features is preferably based on processing microbiome composition data and/or microbiome functional diversity data according to one or more computer-implemented rules (e.g., a feature-selection rule, a user preference rule, etc.), but features can be determined based on any suitable information. Block S132 and/or other portions of the method 100 preferably include applying computer-implemented rules to process population-level data, but can additionally or alternatively include applying computer-implemented rules to process microbiome-related data on a demographic-specific basis (e.g., subgroups sharing a demographic feature such as oral hygiene regimens, ethnicity, age, gender, etc.), condition-specific basis (e.g., subgroups exhibiting a particular mouth-associated condition), a sample type-specific basis (e.g., applying different computer-implemented rules to process microbiome data derived from mouth samples versus fecal matter samples), and/or any other suitable basis. As such, Block S132 can include assigning users from the population of users to one or more subgroups; and applying different computer-implemented rules for determining features (e.g., the set of feature types used; the types of characterization models generated from the features; etc.) for the different subgroups.

In a variation, Block S132 can include applying feature-selection rules (e.g., feature selection algorithms such as exhaustive, best first, simulated annealing, greedy forward, greedy backward, and/or other suitable feature selection algorithms) to filter, rank, and/or otherwise select features for use in generating one or more characterization models (e.g., using mouth-associated feature-selection rules correlating one or more mouth-associated conditions to microbiome composition features and/or microbiome functional diversity features, etc.), therapy models (e.g., using rules correlating one or more therapies to one or more microbiome composition features, microbiome functional diversity features, and/or features derived from characterizations generated in Block S160, etc.), and/or other suitable models. Features (e.g., a feature set) are preferably generated based on evaluating a microbiome dataset against one or more feature-selection rules (e.g., applying the feature-selection rules to the microbiome dataset), but can otherwise be generated. The feature-selection rules can include one or more of: application of statistical analysis operations (e.g., an analysis of probability distributions, etc.), supplementary dataset-based feature-selection rules (e.g., selecting features correlated with supplementary dataset informative of a mouth-associated condition, etc.), processing-based feature-selection rules (e.g., selecting amount and/or type of features based on processing efficiency and/or other processing constraints, etc.), accuracy-based feature-selection rules (e.g., filtering irrelevant and/or redundant features in relation to the mouth-associated condition, etc.), user-selected feature-selection rules, and/or any other suitable feature-selection rules. Choice of feature selection rules can be based on user demographics, mouth-associated conditions, model type, purpose of the model (e.g., efficiency in determining a mouth-associated characterization; accuracy; and/or other suitable criteria, which can be determined based on user preferences, etc.), and/or any other suitable criteria. For example, Block S132 can include applying a first set of feature-selection rules to define a first feature subset (e.g., a comprehensive feature subset operable to be used in generating a characterization model purposed for accuracy over speed) for users with periodontal disease (e.g., determined from supplementary data); and applying a second set of feature-selection rules to define a second feature subset (e.g., a sparse feature subset operable to be used in generating a characterization model purposed for speed), for users with halitosis. However, any suitable number and/or type of feature-selection rules can be applied in any manner to define one or more feature sets.

For example, in Block S132, feature-selection rules can include application of a statistical analysis (e.g., an analysis of probability distributions) of similarities and/or differences between a first group of subjects exhibiting a target state (e.g., a health condition state) and a second group of subjects not exhibiting the target state (e.g., a "normal" state). In implementing this variation, one or more of a Kolmogorov-Smirnov (KS) test, a permutation test, a Cramer-von Mises test, and any other statistical test (e.g., t-test, z-test, chi-squared test, test associated with distributions, etc.) can be used. In particular, one or more such statistical hypothesis tests can be used to assess a set of features having varying degrees of abundance in a first group of subjects exhibiting a target state (e.g., a sick state) and a second group of subjects not exhibiting the target state (e.g., having a normal state). In more detail, the set of features assessed can be constrained based upon percent abundance and/or any other suitable parameter pertaining to diversity in association with the first group of subjects and the second group of subjects, in order to increase or decrease confidence in the characterization. In a specific implementation of this example, a feature can be derived from a taxon of bacteria that is abundant in a certain percentage of subjects of the first group and subjects of the second group, where a relative abundance of the taxon between the first group of subjects and the second group of subjects can be determined from the KS test, with an indication of significance (e.g., in terms of p-value). Thus, an output of Block S132 can include a normalized relative abundance value (e.g., 25% greater abundance of a taxon in sick subjects vs. healthy subjects) with an indication of significance (e.g., a p-value of 0.0013). Variations of feature generation can additionally or alternatively implement or be derived from functional features or metadata features (e.g., non-bacterial markers)

In another variation, Block S132 can additionally or alternatively transform input data from at least one of the microbiome composition diversity dataset and microbiome functional diversity dataset into feature vectors that can be tested for efficacy in predicting characterizations of the population of subjects. Data from the supplementary dataset can be used to provide indication of one or more characterizations of a set of characterizations, where the characterization process is trained with a training dataset of candidate features and candidate classifications to identify features and/or feature combinations that have high degrees (or low degrees) of predictive power in accurately predicting a classification. As such, refinement of the characterization process with the training dataset identifies feature sets (e.g., of subject features, of combinations of features) having high correlation with specific classifications of subjects.

In variations of Block S132, feature vectors effective in predicting classifications of the characterization process can include features related to one or more of: microbiome diversity metrics (e.g., in relation to distribution across taxonomic groups, in relation to distribution across archaeal, bacterial, viral, and/or eukaryotic groups), presence of taxonomic groups in one's microbiome, representation of specific genetic sequences (e.g., 16S sequences) in one's microbiome, relative abundance of taxonomic groups in one's microbiome, microbiome resilience metrics (e.g., in response to a perturbation determined from the supplementary dataset), abundance of genes that encode proteins or RNAs with given functions (enzymes, transporters, proteins from the immune system, hormones, interference RNAs, etc.) and any other suitable features derived from the microbiome diversity dataset and/or the supplementary dataset. For example, Block S132 can include generating a set of microbiome feature vectors (e.g., a feature vector for each user of subgroup or population of users) based on microbiome composition features (e.g., a subset selected based on feature-selection rules), microbiome functional diversity features (e.g., a subset selected based on feature-selection rules), and supplementary features (e.g., biometric features derived from the supplementary biometric sensor data such as image data associated with mouth-associated conditions for the set of users, etc.), where the set of microbiome feature vectors can be used in training the characterizations model and/or other suitable models. Additionally or alternatively, combinations of features can be used in a feature vector, where features can be grouped and/or weighted in providing a combined feature as part of a feature set. For example, one feature or feature set can include a weighted composite of the number of represented classes of bacteria in one's microbiome, presence of a specific genus of bacteria in one's microbiome, representation of a specific 16S sequence in one's microbiome, and relative abundance of a first phylum over a second phylum of bacteria. However, feature vectors and features can be determined in any other suitable manner.

Block S130 can additionally or alternatively include Block S134: generating a characterization model. Block S132 functions to generate one or more characterization models for mouth-associated conditions based on applying one or more features and/or supplementary data. Characterization models (and/or therapy models or other suitable models) can include any one or more of: probabilistic properties, heuristic properties, deterministic properties, and/or any other suitable properties. Block S134 and/or any other suitable portions of the method 100 (e.g., generating a therapy model S140) can employ one or more algorithms analogous to those described in U.S. application Ser. No. 15/374,890 filed 9 Dec. 2016, which is incorporated in its entirety by this reference, but any suitable algorithms can be employed.

Figure 3:
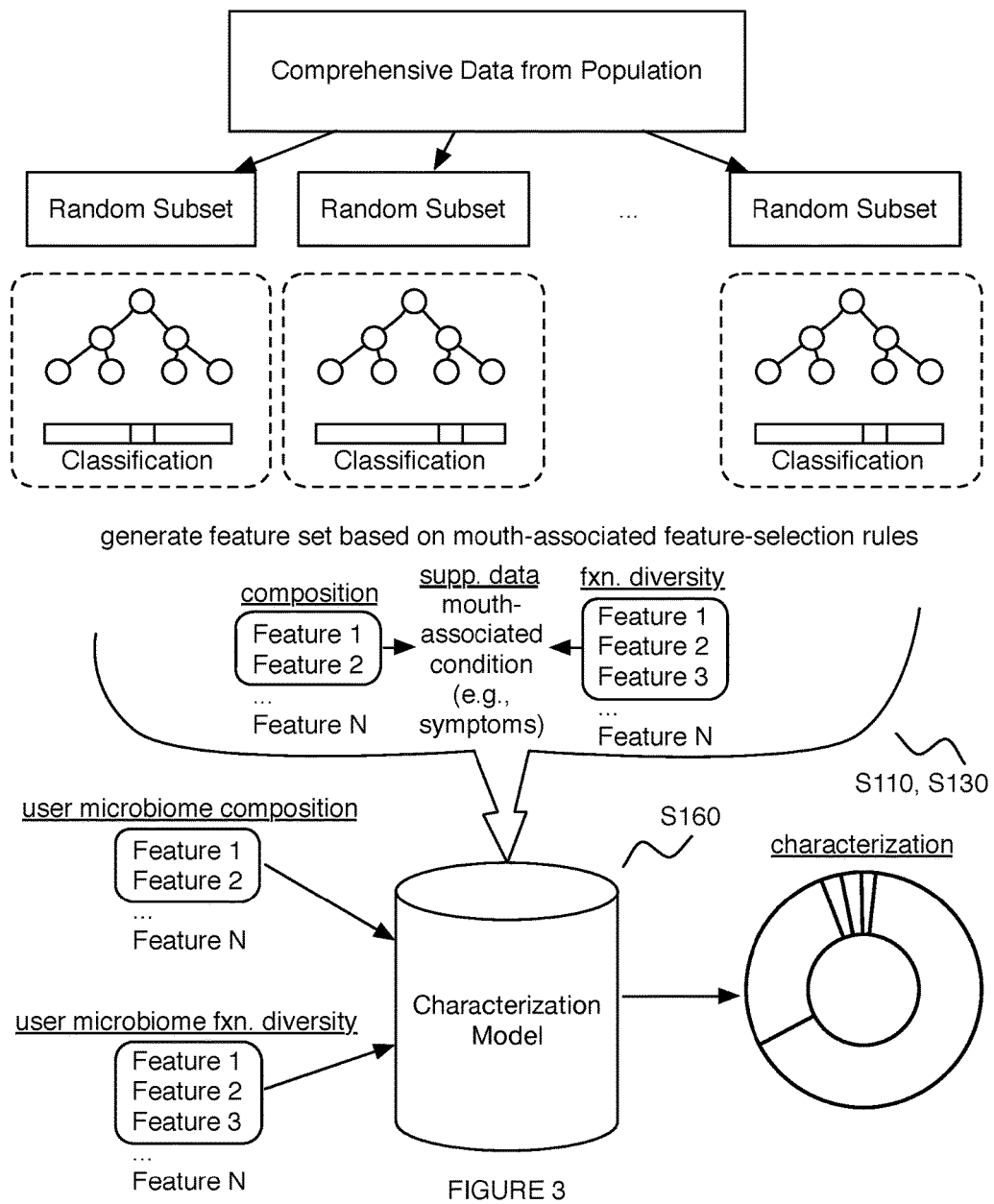
FIG. 3 depicts a schematic representation of a variation of generating and applying a characterization model in an embodiment of a method for microbiome characterization.

As shown in FIG. 3, in an example of Block S134, a characterization model can be generated and trained according to a random forest predictor (RFP) algorithm that combines bagging (e.g., bootstrap aggregation) and selection of random sets of features from a training dataset to construct a set of decision trees, T, associated with the random sets of features. In using a random forest algorithm, N cases from the set of decision trees are sampled at random with replacement to create a subset of decision trees, and for each node, m prediction features are selected from all of the prediction features for assessment. The prediction feature that provides the best split at the node (e.g., according to an objective function) is used to perform the split (e.g., as a bifurcation at the node, as a trifurcation at the node). By sampling many times from a large dataset, the strength of the characterization process, in identifying features that are strong in predicting classifications can be increased substantially. In this example, measures to prevent bias (e.g., sampling bias) and/or account for an amount of bias can be included during processing to increase robustness of the model.

In another example, Block S134 can include generating a neural network model (e.g., a convolutional neural network model), where microbiome composition features, microbiome functional diversity features, supplementary features (e.g., pixel values from images of mouths of users), and/or other suitable features can be used in the neural input layer of the neural network. In another example, Block S134 can include applying an ensemble approach for using a plurality of characterization models (e.g., predicting a plurality of probabilities for diagnosis of a mouth-associated condition using a plurality of characterization models, and using the plurality of probabilities to predict a final diagnosis with a final characterization model, etc.). In another example, privileged information machine learning models (e.g., SVM+, etc.) can be used in training characterization models leveraging additional types of information supplied in the training data (e.g., where more supplementary data is provided by the initial population of users compared to a new test subject).

In a variation of Block S134, a characterization model based upon statistical analyses can identify the sets of features that have the highest correlations with mouth-associated conditions for which one or more therapies would have a positive effect, based upon a random forest predictor algorithm trained with a training dataset derived from a subset of the population of subjects, and validated with a validation dataset derived from a subset of the population of subjects. Thus, characterization of the subject includes characterization of the subject as someone with a mouth-associated condition based upon detection of one or more of the above features, in a manner that is an alternative or supplemental to typical methods of diagnosis. In variations of the specific example, the set of features can, however, include any other suitable features useful for diagnostics. Characterization of the subject(s) can additionally or alternatively implement use of a high false positive test and/or a high false negative test to further analyze sensitivity of the characterization process in supporting analyses generated according to embodiments of the method 100.

Figure 5:
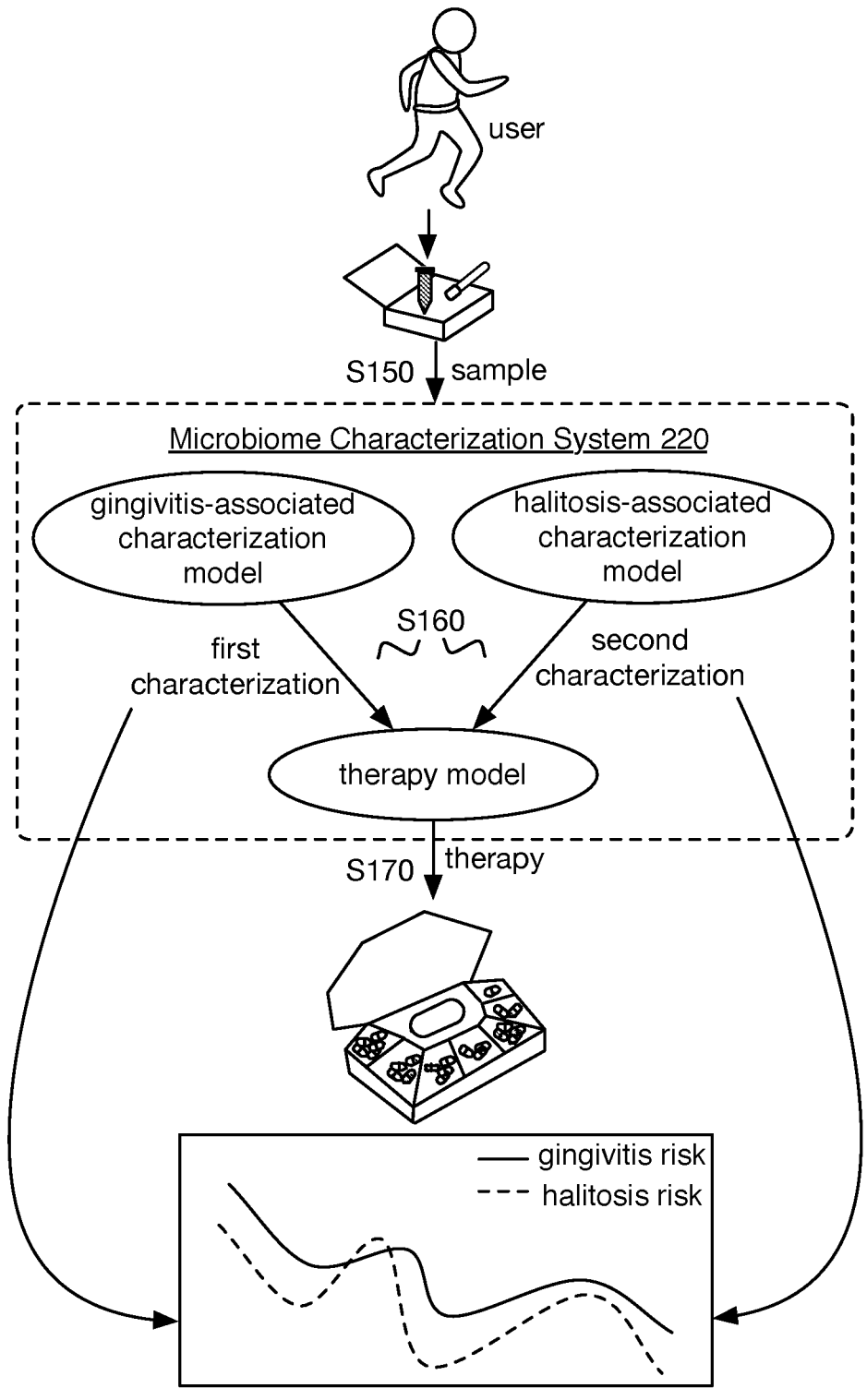
FIG. 5 depicts a variation of applying multiple characterization models in an embodiment of a method for microbiome characterization.

In another variation of Block S134, different characterization models can be generated for different demographic groups (e.g., a first characterization model characterizing a mouth-associated condition for users with high blood sugar levels, a second characterization model for users with normal blood sugar levels, etc.), mouth-associated conditions, individual subjects, supplementary data (e.g., models incorporating features derived from biometric sensor data vs. models independent of supplementary data, etc.), and/or other suitable criteria. In an example, Block S134 can include generating a gingivitis-associated characterization model for characterizing gingivitis-associated conditions (e.g., based on a first feature set derived from at least one of a microbiome composition dataset and a microbiome functional diversity dataset, etc.); generating a halitosis-associated characterization model for characterizing halitosis-associated conditions (e.g., based on a second feature set derived from at least one of the microbiome composition dataset and the microbiome functional diversity dataset, and/or different microbiome datasets, etc.). As shown in FIG. 5, characterizations outputted from different characterization models can be used in determining and/or promoting a therapy, such as by inputting features derived from a first characterization (e.g., output by the gingivitis-associated characterization model) and a second characterization (e.g., output by the halitosis-associated characterization model) into a therapy model (e.g., to generate a therapy tailored to treating both the gingivitis-associated condition and the halitosis-associated condition, etc.).

In another example, Block S134 can include generating a characterization model for a demographic group of users who brush their teeth at least once a day; associating the characterization model with user accounts (e.g., at a database of the microbiome characterization system) for users who indicate that they brush their teeth at least once a day (e.g., at a digital survey presented by the interface); and retrieving the characterization model (e.g., from the database) for characterizing the subjects. Generating a plurality of characterization models suited to different contexts can confer improvements to the microbiome characterization system by improving characterization accuracy (e.g., by tailoring analysis to a particular subject's demographic and/or situation, etc.), retrieval speed for the appropriate characterization model from a database (e.g., by associating customized characterization models with particular user accounts and/or other identifiers), training and/or execution of characterization models (e.g., where the customized models are associated with a subset of a pool of potential features correlated with mouth-associated conditions, and where the remaining unselected features are less correlated with the mouth-associated conditions), and/or other suitable aspects of the microbiome characterization system.

In another variation of Block S134, generating feature sets for different characterization models (and/or therapy models) can be based on different feature selection rules (e.g., obtaining and applying a set of halitosis-associated feature-selection rules correlating the halitosis-associated condition to subsets of microbiome composition features and microbiome functional diversity features, in order to generate a feature set specific to generating a halitosis-associated characterization model). Alternatively, overlapping or the same set of feature selection rules can be used for generating different characterization models (e.g., using the same functional diversity feature in generating two different characterization models for two different user subgroups selected based on frequency of dentist visits, etc.). However, generating any number of characterization models can be performed in any suitable manner.

4.3.C.i Characterization Process—Gingivitis Characterization

In variations of Block S130, performing a characterization process can be for one or more gingivitis-associated conditions. In particular, gingivitis can be a mild gum disease characterized by irritated, swollen and reddened gums, primarily caused by bad oral hygiene, and when not treated, can lead to the more severe disease periodontitis. In addition, gingivitis-associated conditions can be associated with specific microbiota diversity and/or health conditions related to relative abundance of gut microorganisms, and/or microbiome functional diversity.

In variations of Block S130, a set of features useful for characterizations of gingivitis-associated conditions and/or other mouth-associated conditions can include features derived from one or more of the following taxa: *Spirochaetes*, Firmicutes, Proteobacteria, Actinobacteria, Fusobacteria, Bacteroidetes, TM7, Chloroflexi, Tenericutes, Elusimicrobia, Synergistetes, *Porphyromonas gingivalis, Tannerella forsythia, Treponema detnicola, Streptococcus, Rothia, Actinomyces, Haemophilus, Lautropia, Leptotrichia, Prevotella, Porphyromonas, Selenomonas, Peptococcus, Catonella, Eubacterium*, and/or any other suitable taxa.

Additionally or alternatively, in Block S130, the set of features can include functional features associated with gingivitis-associated conditions (e.g., associated with gingivitis diagnostics using mouth samples) and/or other mouth-associated conditions, including one or more of: sulfur relay system (KEGG3), restriction enzyme (KEGG3), and/or any other suitable combination of features. However, performing the characterization process for gingivitis-associated conditions can be performed in any suitable manner using any suitable features (e.g., described herein).

4.3.C.ii Characterization Process—Halitosis Characterization.

In variations of Block S130, performing a characterization process can be for one or more halitosis-associated conditions. In particular, halitosis can be characterized by bad odor of the exhaled breath, such as caused by subgingival bacteria. In addition, halitosis-associated conditions can be associated with specific microbiota diversity and/or health conditions related to relative abundance of gut microorganisms, and/or microbiome functional diversity. In variations of the characterization process of Block S130, a set of features useful for characterizations of halitosis-associated conditions and/or other mouth-associated conditions can include features derived from one or more of the following taxa: *Oribacterium* (Genus), Bacteroidia (Class), Flavobacteriia (Class), Erysipelotrichia (Class), Epsilonproteobacteria (Class), Clostridia (Class), Coriobacteriaceae (Family), Flavobacteriaceae (Family), Porphyromonadaceae (Family), Erysipelotrichaceae (Family), Peptostreptococcaceae (Family), Lachnospiraceae (Family), Campylobacteraceae (Family), Fusobacteriaceae (Family), Streptococcaceae (Family), *Alloprevotella* (Genus), *Capnocytophaga* (Genus), *Porphyromonas* (Genus), *Stomatobaculum* (Genus), *Kingella* (Genus), *Campylobacter* (Genus), *Aggregatibacter* (Genus), *Bergeyella* (Genus), *Lachnoanaerobaculum* (Genus), *Fusobacterium* (Genus), *Peptostreptococcus* (Genus), Coriobacteriales (Order), Bacteroidales (Order), Flavobacteriales (Order), Erysipelotrichales (Order), Campylobacterales (Order), Clostridiales (Order), Lactobacillales (Order), Bacteroidetes (Phylum), Candidatus Saccharibacteria (Phylum), *Neisseria elongata* (Species), *Bergeyella* sp. AF14 (Species), *Capnocytophaga sputigena* (Species), *Peptostreptococcus stomatis* (Species), *Kingella oralis* (Species), *Prevotella nigrescens* (Species), *Porphyromonas catoniae* (Species), and/or any other suitable taxa, where sampling of subjects can involve sampling of the mouth and/or other body region. Additionally or alternatively, features useful for diagnostics associated with halitosis can include features derived from one or more of the following taxa: Negativicutes (Class), Clostridiales Family XI, Incertae Sedis (Family), and/or one of the following functional features: Energy Metabolism (KEGG2), Immune System Diseases (KEGG2), Fatty acid biosynthesis (KEGG3), Carbon fixation pathways in prokaryotes (KEGG3), Selenocompound metabolism (KEGG3), Protein kinases (KEGG3), Energy metabolism (KEGG3), Glycerophospholipid metabolism (KEGG3), Inorganic ion transport and metabolism (KEGG3), Amino acid related enzymes (KEGG3), Carbon fixation in photosynthetic organisms (KEGG3), where sampling of subjects can involve sampling of the gut and/or any other body region.

Additionally or alternatively, in Block S130, the set of features can include functional features associated with halitosis-associated conditions (e.g., associated with halitosis diagnostics using mouth samples) and/or other mouth-associated conditions, including one or more of: cysteine degradation, transsulfuration pathway, odiferous volatile sulphur compound generation, methionine degradation, tryptophan degradation, arginine degradation, lysine degradation, and/or any other suitable combination of features. However, performing the characterization process for halitosis-associated conditions can be performed in any suitable manner using any suitable features (e.g., described herein).

4.4 Method—Personalization to a Subject

Figure 6:
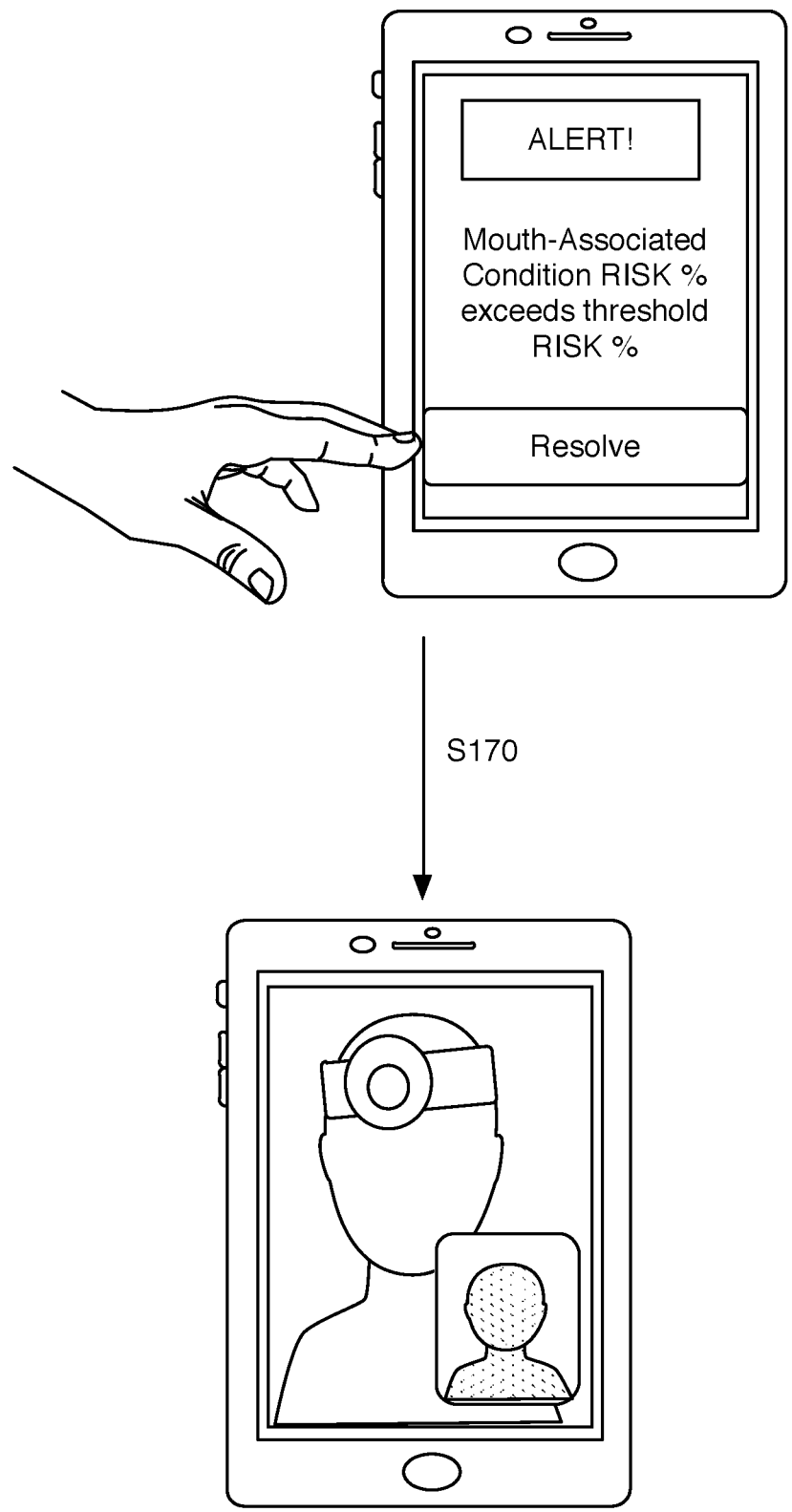
FIG. 6 depicts a variation of promoting a telemedicine therapy in an embodiment of a method for microbiome characterization.

The method 100 can additionally or alternatively include Block S140, which recites: determining a therapy for preventing, ameliorating, and/or otherwise modifying a mouth-associated condition. Block S140 functions to identify and/or predict therapies (e.g., probiotic-based therapies, phage-based therapies, small molecule-based therapies, etc.) that can shift a subject's microbiome composition and/or functional features toward a desired equilibrium state in promotion of the subject's health. Block S140 can additionally or alternatively include generating and/or applying a therapy model for determining the therapy. In Block S140, the therapies can be selected from therapies including one or more of: probiotic therapies (e.g., milk drinks with *Lactobacillus casei, Streptococcus salivarius*, etc.) phage-based therapies, small molecule-based therapies, cognitive/behavioral therapies, physical rehabilitation therapies, clinical therapies, medication-based therapies, diet-related therapies (e.g., reducing sugar intake), and/or any other suitable therapy designed to operate in any other suitable manner in promoting a user's health. In a specific example of a bacteriophage-based therapy, one or more populations (e.g., in terms of colony forming units) of bacteriophages specific to a certain bacteria (or other microorganism) represented in the subject can be used to down-regulate or otherwise eliminate populations of the certain bacteria. As such, bacteriophage-based therapies can be used to reduce the size(s) of the undesired population(s) of bacteria represented in the subject. Complementarily, bacteriophage-based therapies can be used to increase the relative abundances of bacterial populations not targeted by the bacteriophage(s) used. In another specific example, Block S140 can include facilitating an interaction between a user and a care provider (e.g., scheduling an appointment with a care provider; initiating a telemedicine conference over a wireless communication channel, as shown in FIG. 6; etc.), such as in response to and/or concurrently with a trigger condition (e.g., characterizing a mouth-associated condition risk exceeding a threshold; manual request by a user or care provider; identifying an effectiveness score below a threshold based on analysis of post-therapy biological samples; etc.).

Figure 7:
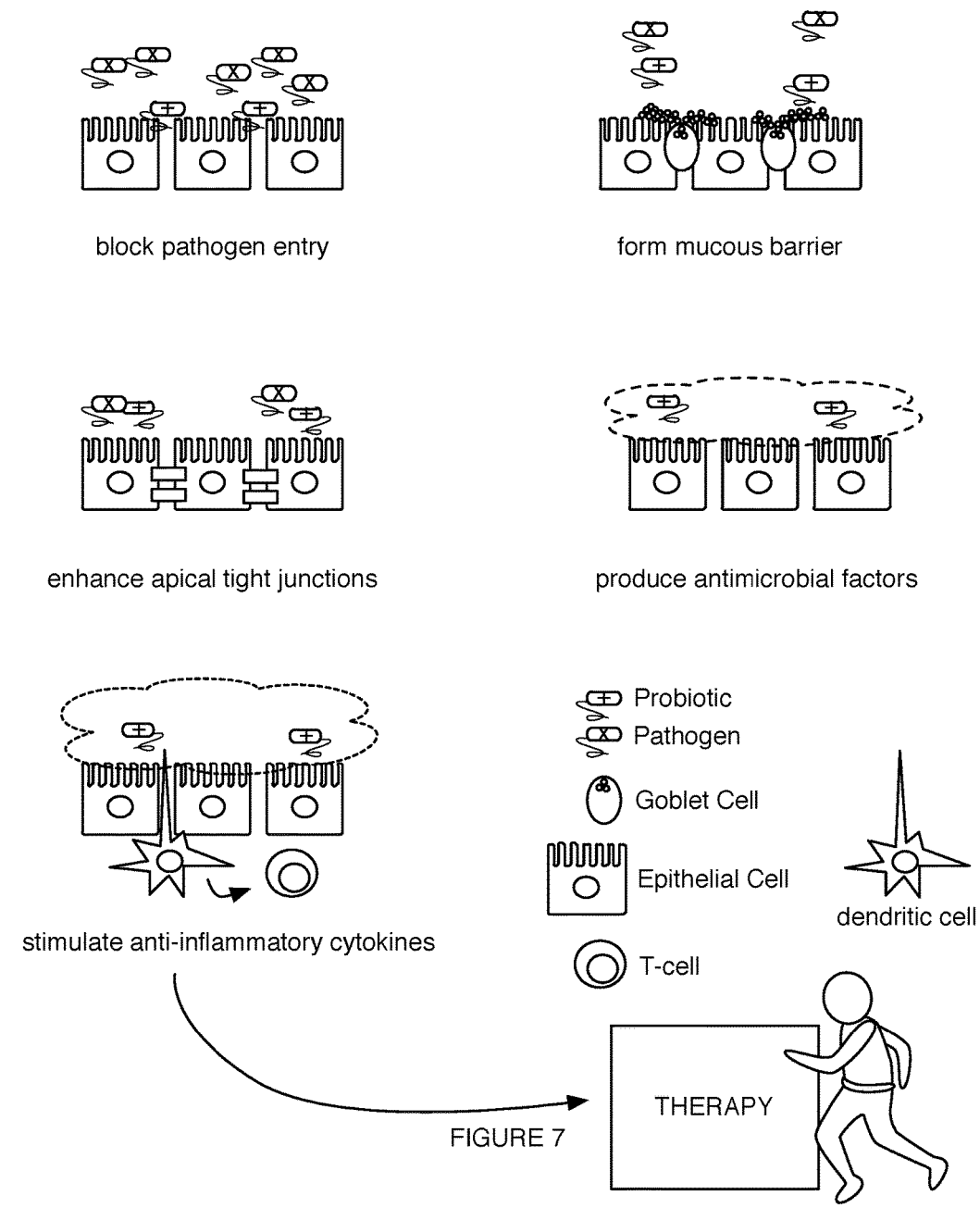
FIG. 7 depicts variations of mechanisms by which probiotic-based therapies operate in an embodiment of a method for microbiome characterization.

Regarding Block S140, in another specific example of probiotic therapies, as shown in FIG. 7, candidate therapies of the therapy model can perform one or more of: blocking pathogen entry into an epithelial cell by providing a physical barrier (e.g., by way of colonization resistance), inducing formation of a mucous barrier by stimulation of goblet cells, enhance integrity of apical tight junctions between epithelial cells of a subject (e.g., by stimulating up regulation of zona-occludens 1, by preventing tight junction protein redistribution), producing antimicrobial factors, stimulating production of anti-inflammatory cytokines (e.g., by signaling of dendritic cells and induction of regulatory T-cells), triggering an immune response, and performing any other suitable function that adjusts a subject's microbiome away from a state of dysbiosis. In variations, Block S140 can include generating a therapy model based upon data (e.g., microbiome data, supplementary data) from a large population of subjects, which can include the population of subjects from which the microbiome datasets are derived in Block S110, where microbiome composition and/or functional features or states of health, prior exposure to and post exposure to a variety of therapeutic measures, are well characterized. Additionally or alternatively, generating (and/or applying) a therapy model can be based on characterizations outputted from one or more characterization models. Therapy models can be used in identifying therapeutic measures that provide desired outcomes for subjects based upon different microbiome characterizations. In an example, support vector machines, as a supervised machine learning algorithm, can be used to generate the therapy model. However, any suitable algorithms and/or approaches can be used in facilitating generation of the therapy model.

Regarding Block S140, processing of therapy models can be analogous to processing of characterization models (e.g., described for Block S130), where any number and/or types of treatment models can be generated for different purposes (e.g., different demographic groups, individuals, supplementary datasets, etc.), associated with user accounts and/or other identifiers, and/or otherwise processed for customizing therapy determination and/or promotion for different subjects. In a variation, Block S140 can include generating different types of therapy models (e.g., trained using different features; generated with different algorithms; etc.) for different therapy types (e.g., a probiotics therapy model for selecting different microorganism species appropriate for treating particular mouth-associated conditions; a medication model for selecting different medications; a home therapy model for users preferring home remedies; etc.). In another variation, the therapy model can be derived in relation to identification of a "normal" or baseline microbiome composition and/or functional features, as assessed from subjects of a population of subjects who are identified to be in good health. Upon identification of a subset of subjects of the population of subjects who are characterized to be in good health (e.g., using features of the characterization process), therapies that modulate microbiome compositions and/or functional features toward those of subjects in good health can be generated in Block S140. Block S140 can thus include identification of one or more baseline microbiome compositions and/or functional features (e.g., one baseline microbiome for each of a set of demographics), and potential therapy formulations and therapy regimens that can shift microbiomes of subjects who are in a state of dysbiosis toward one of the identified baseline microbiome compositions and/or functional features. The therapy model can, however, be generated and/or refined in any other suitable manner.

Regarding Block S140, microorganism compositions associated with probiotic therapies associated with the therapy model preferably include microorganisms that are culturable (e.g., able to be expanded to provide a scalable therapy) and non-lethal (e.g., non-lethal in their desired therapeutic dosages). Furthermore, microorganism compositions can include a single type of microorganism that has an acute or moderated effect upon a subject's microbiome. Additionally or alternatively, microorganism compositions can include balanced combinations of multiple types of microorganisms that are configured to cooperate with each other in driving a subject's microbiome toward a desired state. For instance, a combination of multiple types of bacteria in a probiotic therapy can include a first bacteria type that generates products that are used by a second bacteria type that has a strong effect in positively affecting a subject's microbiome. Additionally or alternatively, a combination of multiple types of bacteria in a probiotic therapy can include several bacteria types that produce proteins with the same functions that positively affect a subject's microbiome.

In relation to Block S140, probiotic compositions can be naturally or synthetically derived. For instance, in one application, a probiotic composition can be naturally derived from fecal matter or other biological matter (e.g., of one or more subjects having a baseline microbiome composition and/or functional features, as identified using the characterization process and the therapy model). Additionally or alternatively, probiotic compositions can be synthetically derived (e.g., derived using a benchtop method) based upon a baseline microbiome composition and/or functional features, as identified using the characterization process and the therapy model. In variations, microorganism agents that can be used in probiotic therapies can include one or more of: yeast (e.g., *Saccharomyces boulardii*), gram-negative bacteria (e.g., *E. coli* Nissle), gram-positive bacteria (e.g., *Bifidobacteria bifidum, Bifidobacteria infantis, Lactobacillus rhamnosus, Lactococcus lactis, Lactobacillus plantarum, Lactobacillus acidophilus, Lactobacillus casei, Bacillus polyfermenticus*, etc.), and any other suitable type of microorganism agent.

In a variation of Block S140, for subjects who exhibit gingivitis, a probiotic therapy can include a combination of one or more of: *Spirochaetes* provided at dosages of 3-9 billion CFU per doses, as determined from a therapy model that predicts positive adjustment of a patient's microbiome in response to the therapy. In another variation, for subjects exhibiting a halitosis-associated condition, a probiotic therapy can include a combination of one or more of: *Oribacterium* provided at dosages of 3-9 billion CFU per doses, as determined from a therapy model that predicts positive adjustment of a patient's microbiome in response to the therapy. In specific examples, a subject can be instructed to ingest capsules including the probiotic formulation according to a regimen tailored to one or more of his/her: physiology (e.g., body mass index, weight, height), demographics (e.g., gender, age), severity of dysbiosis, sensitivity to medications, and any other suitable factor.

The method 100 can additionally or alternatively include Block S150, which recites: processing a biological sample from a user (e.g., subject). Block S150 functions to facilitate generation of a microbiome dataset (e.g., microbiome composition dataset, microbiome functional diversity dataset, etc.) for the subject that can be used to derive inputs for the characterization process. In Block S150, the biological sample is preferably generated from the subject and/or an environment of the subject in a non-invasive manner. In variations, non-invasive manners of sample reception can use any one or more of: an interdental brush to sample subgingival microorganisms and/or supragingival microorganisms, a permeable substrate (e.g., a swab configured to wipe a region of a subject's body, toilet paper, a sponge, etc.), a non-permeable substrate (e.g., a slide, tape, etc.) a container (e.g., vial, tube, bag, etc.) configured to receive a sample from a region of a subject's body, and any other suitable sample-reception element. In a specific example, the biological sample can be collected from one or more of the subject's nose, skin, genitals, mouth, and/or gut in a non-invasive manner (e.g., using a swab and a vial). However, the biological sample can additionally or alternatively be received in a semi-invasive manner or an invasive manner. In variations, invasive manners of sample reception can use any one or more of: a needle, a syringe, a biopsy element, a lance, and any other suitable instrument for collection of a sample in a semi-invasive or invasive manner. In specific examples, samples can include blood samples, plasma/serum samples (e.g., to enable extraction of cell-free DNA), tissue samples, and/or any other samples. Regarding Block S150, in the above variations and examples, the biological sample can be taken from any suitable body region.

Furthermore, in Block S150, processing and analyzing the biological sample from the subject is preferably performed in a manner similar to that of one of the embodiments, variations, and/or examples of sample processing described in relation to Block S110 above, and/or in U.S. application Ser. No. 15/374,890 filed 9 Dec. 2016, which is incorporated in its entirety by this reference. However, biological sample reception and processing in Block S150 can alternatively be performed in any other suitable manner.

The method 100 can additionally or alternatively include Block S160, which recites: determining a characterization of the subject based upon processing a microbiome dataset derived from the biological sample, with the characterization process. Block S160 functions to extract features from microbiome-derived data of the subject, and use the features as inputs into an embodiment, variation, or example of the characterization process (e.g., a characterization model) described in Block S130 above. Determining the characterization in Block S160 thus preferably includes identifying features and/or combinations of features associated with the microbiome composition and/or functional features of the subject, inputting the features into the characterization process, and receiving an output that characterizes the subject as belonging to one or more of: a behavioral group, a gender group, a dietary group, a disease-state group, and any other suitable group capable of being identified by the characterization process. Block S160 can further include generation of and/or output of a confidence metric associated with the characterization of the subject. For instance, a confidence metric can be derived from the number of features used to generate the characterization, relative weights or rankings of features used to generate the characterization, measures of bias in the characterization process, and/or any other suitable parameter associated with aspects of the characterization process. In some variations of Block S160, features extracted from the microbiome dataset of the subject can be supplemented with survey-derived and/or medical history-derived features from the subject, which can be used to further refine the characterization process of Block S130.

In a variation, Block S160 can include generating values for features selected based on feature-selection rules (e.g., mouth-associated feature-selection rules), and using the values to characterize the subject. Such processes can confer improvements in the microbiome characterization system by improving feature extraction processing speed by extracting only a subset of a set of features (e.g., microbiome composition features, microbiome functional diversity features, etc.) based on feature-selection rules (e.g., used in determining the subset of features used in training the corresponding characterization model), rather than generating each feature of the set of features. In another variation, Block S160 can include characterizing one or more risks (e.g., of exhibiting; of contracting; of showing symptoms regarding; etc.) of a mouth-associated condition. For example, the method 100 can include characterizing at least one of a gingivitis risk and a halitosis risk with one or more characterization models, and promoting a therapy operable to facilitate modification of a microbiome composition and/or a microbiome functional diversity of the user to reduce at least one of the gingivitis risk and the halitosis risk. However, characterizing risks can be performed in any suitable manner. In another variation, Block S160 can include diagnosing a cause of a mouth-associated condition and/or associated risks. For example, the method 100 can include: receiving user supplementary data informative of the mouth-associated condition in relation to the user; determining a cause for the at least one of the gingivitis risk and the halitosis risk based on the user supplementary data (e.g., along with user microbiome composition features and/or user microbiome functional diversity features, such as those used in determining the characterization for the user); and/or determining a therapy based on the cause. However, diagnosing causes can be performed in any suitable manner.

Figure 4:
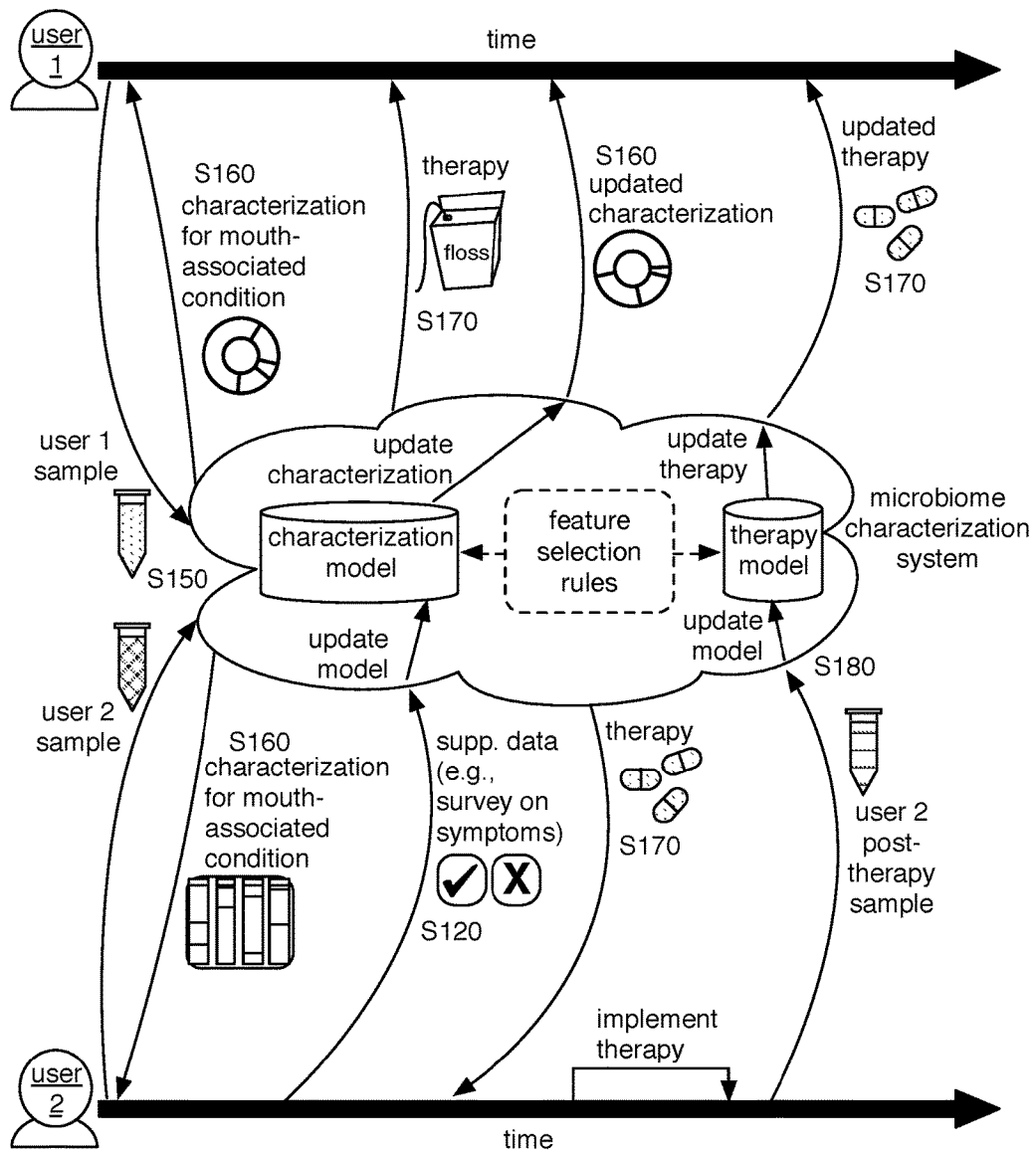
FIG. 4 depicts a variation of applying and updating a characterization model and a therapy model in an embodiment of a method for microbiome characterization.

In another variation, Block S160 can include determining a characterization with an updated characterization model. Updating one or more characterization models is preferably based on updated user supplementary data (e.g., received by a user device associated with the user; sharing any supplementary data types described in Block S120, etc.) and a user feature set (e.g., user microbiome composition features and/or user microbiome functional diversity features used in determining the characterization; etc.), but can be based on any suitable data. In a specific example, the method 100 can include: determining a characterization for a user based on a characterization model and a processed biological sample from the user; receiving a survey response from at least one of the user and a care provider (e.g., informative of mouth-associated conditions such as gingivitis-related symptoms); and updating the characterization model with the survey response and features used in determining the characterization. Updating a characterization model can trigger one or more of: storing the updated characterization model (e.g., in association with identifiers previously stored with the original characterization model, etc.), updated characterizations with the updated characterization model for one or more users (e.g., transmitting an updated characterization to a user in response to updating the characterization model, as shown in FIG. 4, etc.), updating a therapy based on updated characterizations, other portions of the method 100, and/or other suitable operations. However, updating characterization models and/or performing associated characterizations can be performed in any suitable manner. Further, determining a characterization can be performed in any suitable manner.

4.5 Method—Promoting and Monitoring a Therapy.

Figure 8:
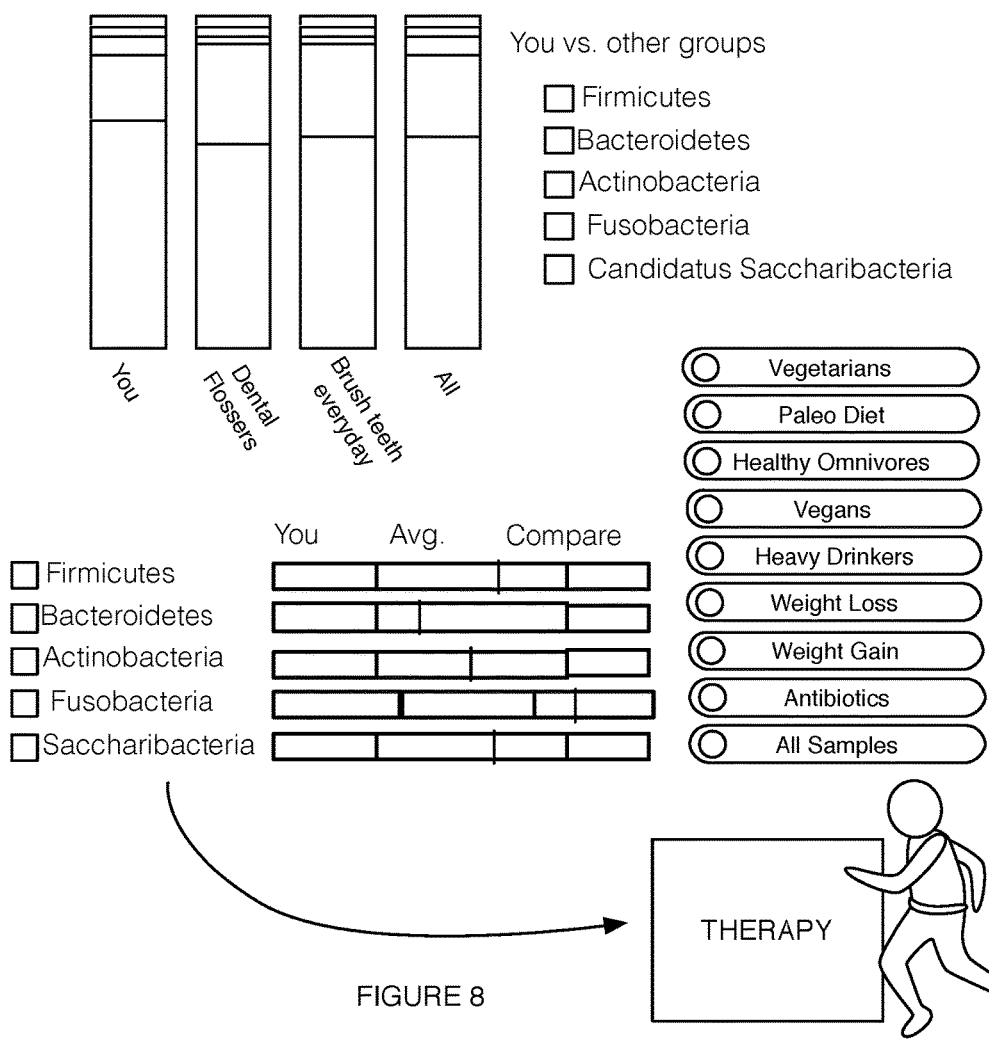
FIG. 8 depicts a variation of notification provision in an embodiment of a method for microbiome characterization.

The method 100 can additionally or alternatively include Block S110, which recites: promoting a therapy to the subject based upon the characterization and the therapy model, which functions to recommend or provide a personalized therapy to the subject, in order to shift the microbiome composition and/or functional features of the subject toward a desired equilibrium state. Block S110 can include provision of a customized therapy to the subject according to their microbiome composition and functional features, as shown in FIG. 8, where the customized therapy is a formulation of microorganisms configured to correct dysbiosis characteristic of subjects having the identified characterization. As such, outputs of Block S140 can be used to directly promote a customized therapy formulation and regimen (e.g., dosage, usage instructions) to the subject based upon a trained therapy model. Additionally or alternatively, therapy provision can include recommendation of available therapeutic measures configured to shift microbiome composition and/or functional features toward a desired state. In variations, available therapeutic measures can include one or more of: consumables (e.g., food items, beverage items, etc.), topical therapies (e.g., lotions, ointments, antiseptics, etc.), nutritional supplements (e.g., vitamins, minerals, fiber, fatty acids, amino acids, prebiotics, etc.), medications, antibiotics, bacteriophages, and any other suitable therapeutic measure. For instance, a combination of commercially available probiotic supplements can include a suitable probiotic therapy for the subject according to an output of the therapy model.

Additionally or alternatively, in a specific example, the therapy of Block S110 can include a bacteriophage-based therapy. In more detail, one or more populations (e.g., in terms of colony forming units) of bacteriophages specific to a certain bacteria (or other microorganism) represented in the subject can be used to down-regulate or otherwise eliminate populations of the certain bacteria. As such, bacteriophage-based therapies can be used to reduce the size(s) of the undesired population(s) of bacteria represented in the subject. Complementarily, bacteriophage-based therapies can be used to increase the relative abundances of bacterial populations not targeted by the bacteriophage(s) used. Therapy provision in Block S110 can include provision of notifications to a subject regarding the recommended therapy and/or other forms of therapy. Types of notifications and manners of providing notifications can be analogous to that described in U.S. application Ser. No. 15/374,890 filed 9 Dec. 2016, which is incorporated in its entirety by this reference The method 100 can additionally or alternatively include Block S180, which recites: monitoring effectiveness of the therapy for the subject, based upon processing biological samples, to assess microbiome composition and/or functional features for the subject at a set of time points associated with the probiotic therapy. Block S180 functions to gather additional data regarding positive effects, negative effects, and/or lack of effectiveness of a probiotic therapy suggested by the therapy model for subjects of a given characterization, where the additional data can be used, for example, to generate, update, and/or execute one or more characterization models, therapy models, and/or other suitable models. For example, as shown in FIG. 4, the method 100 can include: updating the therapy model based on the therapy-influenced modulation of the mouth-associated condition (e.g., modulation based on comparison of a pre- and post-therapy characterization); in response to updating the therapy model, updating a therapy for a user based on the updated therapy model; and; promoting the therapy to the user. However, any suitable portion of the method 100 and/or any suitable operation can be performed in response to updating of models. Monitoring of a subject during the course of a therapy promoted by the therapy model (e.g., by receiving and analyzing biological samples from the subject throughout therapy, by receiving survey-derived data from the subject throughout therapy) can thus be used to generate a therapy-effectiveness model for each characterization provided by the characterization process of Block S130, and each recommended therapy measure provided in Blocks S140 and S110.

In Block S180, the subject can be prompted to provide additional biological samples at one or more key time points of a therapy regimen that incorporates the therapy, and the additional biological sample(s) can be processed and analyzed (e.g., in a manner similar to that described in relation to Block S110) to generate metrics characterizing modulation of the subject's microbiome composition and/or functional features. For example, the method 100 can include: receiving a post-therapy biological sample (e.g., received after promotion of a therapy) from the user; generating a post-therapy characterization of the user in relation to the mouth-associated condition based on the characterization model and the post-therapy biological sample (e.g., microbiome datasets and/or features derived from processing the post-therapy biological sample); and characterizing modulation of the mouth-associated condition (e.g., change in indices indicative of the mouth-associated condition; change in microbiome composition and/or functional diversity; change in symptoms; change in supplementary data values such as changes in visual appearance of the mouth based on image data; etc.) in relation to the first user based on a comparison between the post-therapy characterization and the pre-therapy characterization. In another example, metrics related to one or more of: a change in relative abundance of one or more taxonomic groups represented in the subject's microbiome at an earlier time point, a change in representation of a specific taxonomic group of the subject's microbiome, a ratio between abundance of a first taxonomic group of bacteria and abundance of a second taxonomic group of bacteria of the subject's microbiome, a change in relative abundance of one or more functional families in a subject's microbiome, and any other suitable metrics can be used to assess therapy effectiveness from changes in microbiome composition and/or functional features. Additionally or alternatively, survey-derived data from the subject, pertaining to experiences of the subject while on the therapy (e.g., experienced side effects, personal assessment of improvement, etc.) can be used to determine effectiveness of the therapy in Block S180. However, monitoring effectiveness of one or more therapies can be performed in any suitable manner.

Any portions of the method 100 and/or instances of a portion of the method 100 can be performed in serial (e.g., in response to, etc.), parallel (e.g., concurrently on different threads for parallel computing to improve system processing ability for characterizing mouth-associated conditions, etc.), and/or with any suitable temporal relationship.

The method 100 can, however, include any other suitable blocks or steps configured to facilitate reception of biological samples from subjects, processing of biological samples from subjects, analyzing data derived from biological samples, and generating models that can be used to provide customized diagnostics and/or probiotic-based therapeutics according to specific microbiome compositions and/or functional features of subjects. The method 100 and/or system of the embodiments can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of a patient computer or mobile device, or any suitable combination thereof. Other systems and methods of the embodiments can be embodied and/or implemented at least in part as a machine configured to receive a computer-readable medium storing computer-readable instructions. The instructions can be executed by computer-executable components integrated by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component can be a processor, though any suitable dedicated hardware device can (alternatively or additionally) execute the instructions.

The FIGURES illustrate the architecture, functionality and operation of possible implementations of systems, methods and computer program products according to preferred embodiments, example configurations, and variations thereof. In this regard, each block in the flowchart or block diagrams may represent a module, segment, step, or portion of code, which includes one or more executable instructions for implementing the specified logical function(s). It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions. The embodiments include every combination and permutation of the various system components and the various method processes, including any variations, examples, and specific examples. As a person skilled in the art will recognize from the previous detailed description and from the figures and claims, modifications and changes can be made to the embodiments of the invention without departing from the scope of this invention as defined in the following claims.

We claim:

1. A system for evaluating a mouth-associated condition in relation to a user, the system comprising:
   a handling network operable to collect containers comprising material from a set of users, the handling network comprising:
      a library preparation system operable to fragment and perform multiplex amplification on the material using a primer compatible with a genetic target associated with the mouth-associated condition;
      a sequencing system operable to determine microorganism sequences from sequencing the material;
   a microbiome characterization system operable to:
      determine microbiome composition data and microbiome functional diversity data based on an alignment between the microorganism sequences and reference sequences associated with the mouth-associated condition,
      collect supplementary data associated with the mouth-associated condition for the set of users, and
      transform the supplementary data and features extracted from the microbiome composition data and the microbiome functional diversity data into a characterization model for the mouth-associated condition; and
   a treatment system operable to provide a treatment to the user based on characterizing the user with the characterization model in relation to the mouth-associated condition.

2. The system of claim 1, wherein the microbiome characterization system is further operable to:
   extract microbiome composition features from the microbiome composition data based on a first mouth-associated feature-selection rule; and
   extract microbiome functional diversity features from the microbiome functional diversity data based on a second mouth-associated feature-selection rule, wherein the features comprise the microbiome composition features and the microbiome functional diversity features.

3. The system of claim 2, wherein the first and the second mouth-associated feature-selection rules improve the microbiome characterization system by facilitating decreased processing time to transform the supplementary data and the features into the characterization model.

4. The system of claim 2, wherein the microbiome functional diversity features comprises at least one of: a cluster of orthologous group of proteins feature, a genomic functional feature, a taxonomic feature, a chemical functional feature, and a systemic functional feature.

5. The system of claim 1, wherein the features comprise Kyoto Encyclopedia of Genes and Genomes (KEGG) functional features associated with at least one of: sulfur relay system, restriction enzyme, energy metabolism, immune system disease, fatty acid biosynthesis, carbon fixation pathways in prokaryotes, selenocompound metabolism, protein kinases, energy metabolism, glycerophospholipid metabolism, inorganic ion transport and metabolism, amino acid related enzymes, and carbon fixation in photosynthetic organisms.

6. The system of claim 5, wherein the features associated with microbiome composition, comprise features derived from at least one of: relative abundance monotonic transformations and non-monotonic transformations.

7. The system of claim 6, wherein transformation of features associated with microbiome composition comprise at least one of: normalizations, features vectors derived from latent variables analyses being linear or not-linear alternatives, linear or non-linear regression, kernel methods, features embedding methods, machine learning and/or statistical inference methods.

8. The system of claim 5, wherein the features comprise a microbiome composition feature associated with a relative abundance of at least of: *Neisseria elongata* and *Bergeyella* sp. AF14.

9. The system of claim 1, further comprising an interface operable to improve display of mouth-associated condition information derived from the characterization model, wherein the mouth-associated condition information comprises a microbiome composition for the user relative to a user group sharing a demographic characteristic, and wherein the microbiome composition comprises taxonomic groups comprising at least one of: *Spirochaetes*, Firmicutes, Proteobacteria, Actinobacteria, Fusobacteria, Bacteroidetes, TM7, Chloroflexi, Tenericutes, Elusimicrobia, Synergistetes, *Porphyromonas gingivalis*, *Tannerella forsythia*,

*Treponema detnicola, Streptococcus, Rothia, Actinomyces, Haemophilus, Lautropia, Leptotrichia, Prevotella, Porphyromonas, Selenomonas, Peptococcus, Catonella, Eubacterium, Oribacterium* (Genus), Bacteroidia (Class), Flavobacteriia (Class), Erysipelotrichia (Class), Epsilonproteobacteria (Class), Clostridia (Class), Coriobacteriaceae (Family), Flavobacteriaceae (Family), Porphyromonadaceae (Family), Erysipelotrichaceae (Family), Peptostreptococcaceae (Family), Lachnospiraceae (Family), Campylobacteraceae (Family), Fusobacteriaceae (Family), Streptococcaceae (Family), *Alloprevotella* (Genus), *Capnocytophaga* (Genus), *Porphyromonas* (Genus), *Stomatobaculum* (Genus), *Kingella* (Genus), *Campylobacter* (Genus), *Aggregatibacter* (Genus), *Bergeyella* (Genus), *Lachnoanaerobaculum* (Genus), *Fusobacterium* (Genus), *Peptostreptococcus* (Genus), Coriobacteriales (Order), Bacteroidales (Order), Flavobacteriales (Order), Erysipelotrichales (Order), Campylobacterales (Order), Clostridiales (Order), Lactobacillales (Order), Bacteroidetes (Phylum), Candidatus Saccharibacteria (Phylum), *Neisseria elongata* (Species), *Bergeyella* sp. AF14 (Species), *Capnocytophaga sputigena* (Species), *Peptostreptococcus stomatis* (Species), *Kingella oralis* (Species), *Prevotella nigrescens* (Species), *Porphyromonas catoniae* (Species), Negativicutes (Class), Clostridiales Family XI, and Incertae Sedis (Family).

10. The system of claim 9, wherein the mouth-associated condition information comprises a risk of infection for the user for at least one of: a gingivitis-associated condition and a halitosis-associated condition, and wherein the treatment is operable to reduce the risk of infection.

11. A method for characterizing a mouth-associated condition in relation to a first user, the method comprising:
  generating a microbiome composition dataset and a microbiome functional diversity dataset based on microorganism sequences derived from biological samples from a set of users, wherein generating the microbiome composition dataset and the microbiome functional diversity dataset comprises:
    identifying primers for nucleic acid sequences associated with the mouth-associated condition,
    fragmenting nucleic acid material,
    amplifying the fragmented nucleic acid material using the identified primers, and
    determining an alignment of the microorganism sequences to reference sequences associated with the mouth-associated condition;
  receiving a supplementary dataset informative of the mouth-associated condition for the set of users;
  obtaining a set of mouth-associated feature-selection rules correlating the mouth-associated condition to a subset of microbiome composition features and a subset of microbiome functional diversity features;
  generating a feature set based on evaluating the microbiome composition dataset and the microbiome functional diversity dataset against the set of mouth-associated feature-selection rules;
  applying the feature set with the supplementary dataset to generate a characterization model for the mouth-associated condition;
  generating a first characterization of the first user in relation to the mouth-associated condition using the characterization model; and
  providing a therapy to the first user based on the first characterization.

12. The method of claim 11, wherein the characterization model is a gingivitis-associated characterization model, the method further comprising:
  generating a second feature set based on the microbiome composition dataset and the microbiome functional diversity dataset;
  applying the second feature set to generate a halitosis-associated characterization model; and
  generating a second characterization of the first user in relation to a halitosis-associated condition using the halitosis-associated characterization model.

13. The method of claim 12, wherein promoting the therapy to the first user is further based on the second characterization.

14. The method of claim 12, wherein generating the second feature set comprises:
  obtaining a set of halitosis-associated feature-selection rules correlating the halitosis-associated condition to a second subset of microbiome composition features and a second subset of microbiome functional diversity features; and
  generating the second feature set based on evaluating the microbiome composition dataset and the microbiome functional diversity dataset against the set of halitosis-associated feature-selection rules.

15. The method of claim 11, further comprising:
  receiving a post-therapy biological sample from the first user;
  generating a post-therapy characterization of the first user in relation to the mouth-associated condition based on the characterization model and the post-therapy biological sample; and
  characterizing modulation of the mouth-associated condition in relation to the first user based on a comparison between the post-therapy characterization and the characterization.

16. The method of claim 15, wherein the therapy is selected based on a therapy model, the method further comprising:
  updating the therapy model based on the modulation of the mouth-associated condition in relation to the first user;
  in response to updating the therapy model, updating a second therapy for a second user based on the updated therapy model; and
  promoting the updated second therapy to the second user.

17. The method of claim 11, wherein the supplementary dataset comprises biometric sensor data informative of the mouth-associated condition, wherein generating the feature set comprises generating a set of microbiome feature vectors based on the subset of microbiome composition features, the subset of microbiome functional diversity features, and a biometric feature derived from the biometric sensor data, and wherein applying the feature set comprises training the characterization model with the set of microbiome feature vectors.

18. The method of claim 17, wherein the biometric sensor data comprises image data associated with the mouth-associated condition for the set of users, and wherein the biometric feature is derived from the image data.

19. The method of claim 11, wherein the characterization comprises at least one of a gingivitis risk and a halitosis risk, and wherein the therapy is operable to facilitate modification of a microbiome composition and a microbiome functional diversity of the first user to reduce the at least one of the gingivitis risk and the halitosis risk.

20. The method of claim 19, wherein generating the first characterization is based on inputting user microbiome composition features and user microbiome functional diversity features into the characterization model, the method further comprising:
  receiving user supplementary data informative of the mouth-associated condition in relation to the first user;
  determining a cause for the at least one of the gingivitis risk and the halitosis risk based on the user supplementary data, the user microbiome composition features, and the user microbiome functional diversity features; and
  determining the therapy based on the cause.

21. The method of claim 20, further comprising:
  updating the characterization model based on the user supplementary data, the user microbiome composition features, and the user microbiome functional diversity features; and
  in response to updating the characterization model, updating a second characterization for a second user based on the updated characterization model.

22. The method of claim 11, wherein the mouth-associated condition comprises a gingivitis-associated condition, and wherein the subset of microbiome composition features comprises a composition feature associated with a set of taxa comprising at least one of: *Spirochaetes*, Firmicutes, Proteobacteria, Actinobacteria, Fusobacteria, Bacteroidetes, TM7, Chloroflexi, Tenericutes, Elusimicrobia, Synergistetes, *Porphyromonas gingivalis*, *Tannerella forsythia*, *Treponema detnicola*, *Streptococcus*, *Rothia*, *Actinomyces*, *Haemophilus*, *Lautropia*, *Leptotrichia*, *Prevotella*, *Porphyromonas*, *Selenomonas*, *Peptococcus*, *Catonella*, and *Eubacterium*.

23. The method of claim 22, wherein the subset of microbiome functional diversity features comprises a Kyoto Encyclopedia of Genes and Genomes (KEGG) functional features associated with at least one of: sulfur relay system and restriction enzyme.

24. The method of claim 11, wherein the mouth-associated condition comprises a halitosis-associated condition, and wherein the subset of microbiome composition features comprises a composition feature associated with a set of taxa comprising at least one of: *Oribacterium* (Genus), Bacteroidia (Class), Flavobacteriia (Class), Erysipelotrichia (Class), Epsilonproteobacteria (Class), Clostridia (Class), Coriobacteriaceae (Family), Flavobacteriaceae (Family), Porphyromonadaceae (Family), Erysipelotrichaceae (Family), Peptostreptococcaceae (Family), Lachnospiraceae (Family), Campylobacteraceae (Family), Fusobacteriaceae (Family), Streptococcaceae (Family), *Alloprevotella* (Genus), *Capnocytophaga* (Genus), *Porphyromonas* (Genus), *Stomatobaculum* (Genus), *Kingella* (Genus), *Campylobacter* (Genus), *Aggregatibacter* (Genus), *Bergeyella* (Genus), *Lachnoanaerobaculum* (Genus), *Fusobacterium* (Genus), *Peptostreptococcus* (Genus), Coriobacteriales (Order), Bacteroidales (Order), Flavobacteriales (Order), Erysipelotrichales (Order), Campylobacterales (Order), Clostridiales (Order), Lactobacillales (Order), Bacteroidetes (Phylum), Candidatus Saccharibacteria (Phylum), *Neisseria elongata* (Species), *Bergeyella* sp. AF14 (Species), *Capnocytophaga sputigena* (Species), *Peptostreptococcus stomatis* (Species), *Kingella oralis* (Species), *Prevotella nigrescens* (Species), *Porphyromonas catoniae* (Species), Negativicutes (Class), Clostridiales Family XI, and Incertae Sedis (Family).

25. The method of claim 24, wherein the subset of microbiome functional diversity features comprises a Kyoto Encyclopedia of Genes and Genomes (KEGG) functional features associated with at least one of: Energy Metabolism, Immune System Diseases, Fatty acid biosynthesis, Carbon fixation pathways in prokaryotes, Selenocompound metabolism, Protein kinases, Energy metabolism, Glycerophospholipid metabolism, Inorganic ion transport and metabolism, Amino acid related enzymes, Carbon fixation in photosynthetic organisms, sulfur relay system, and restriction enzyme.

26. The method of claim 22, wherein the composition feature is associated at least one of: *Neisseria elongata* (Species), *Bergeyella* sp. AF14 (Species), *Capnocytophaga sputigena* (Species), *Peptostreptococcus stomatis* (Species), *Kingella oralis* (Species), *Prevotella nigrescens* (Species), *Porphyromonas catoniae* (Species), *Oribacterium* (Genus), *Alloprevotella* (Genus), *Capnocytophaga* (Genus), *Porphyromonas* (Genus), *Stomatobaculum* (Genus), *Kingella* (Genus), *Campylobacter* (Genus), *Aggregatibacter* (Genus), *Bergeyella* (Genus), *Lachnoanaerobaculum* (Genus), *Fusobacterium* (Genus), *Peptostreptococcus* (Genus).

27. The method of claim 26, wherein the composition feature of a single microorganism is associated with at least one of the following metrics: relative abundance, differential relative abundance, presence, and absence.

* * * * *